United States Patent
Dietze, Jr. et al.

(10) Patent No.: US 8,827,902 B2
(45) Date of Patent: Sep. 9, 2014

(54) SURGICAL INSTRUMENT SYSTEM AND METHOD FOR PROVIDING RETRACTION AND VERTEBRAL DISTRACTION

(76) Inventors: Donald David Dietze, Jr., Lacombe, LA (US); Brian Reed Bankoski, West Grove, PA (US)

( * ) Notice: Subject to any disclaimer, the term of this patent is extended or adjusted under 35 U.S.C. 154(b) by 131 days.

(21) Appl. No.: 13/210,938

(22) Filed: Aug. 16, 2011

(65) Prior Publication Data
US 2012/0041272 A1 Feb. 16, 2012

Related U.S. Application Data

(60) Provisional application No. 61/373,885, filed on Aug. 16, 2010.

(51) Int. Cl.
*A61B 1/32* (2006.01)
*A61B 17/70* (2006.01)
*A61B 17/02* (2006.01)
*A61B 17/00* (2006.01)

(52) U.S. Cl.
CPC ......... *A61B 17/0206* (2013.01); *A61B 17/7065* (2013.01); *A61B 17/0293* (2013.01); *A61B 2017/00915* (2013.01); *A61B 2017/00946* (2013.01); *A61B 17/025* (2013.01); *A61B 2017/00557* (2013.01); *A61B 2017/0262* (2013.01); *A61B 2017/0256* (2013.01)
USPC ............................. 600/215; 600/201; 600/231

(58) Field of Classification Search
CPC ............... A61B 17/02; A61B 17/0206; A61B 17/0218; A61B 17/025; A61B 17/0281; A61B 1/32; A61B 2017/02; A61B 2017/0218; A61B 2017/0237; A61B 2017/0243
USPC ......... 600/201, 204, 206–208, 210, 214, 215, 600/219–234; 606/90, 248, 249
See application file for complete search history.

(56) References Cited

U.S. PATENT DOCUMENTS

| | | | |
|---|---|---|---|
| 6,102,854 A * | 8/2000 | Cartier et al. ................. 600/228 |
| 6,120,436 A * | 9/2000 | Anderson et al. ............. 600/201 |
| 6,206,828 B1 * | 3/2001 | Wright .......................... 600/232 |
| 6,338,712 B2 * | 1/2002 | Spence et al. ................. 600/201 |
| 6,361,492 B1 * | 3/2002 | Santilli ......................... 600/205 |
| 6,837,851 B1 * | 1/2005 | Valentini et al. .............. 600/210 |
| 6,869,398 B2 * | 3/2005 | Obenchain et al. ............ 600/224 |
| 7,056,287 B2 * | 6/2006 | Taylor et al. .................. 600/210 |
| 7,494,463 B2 * | 2/2009 | Nehls ............................ 600/227 |
| 7,537,565 B2 * | 5/2009 | Bass .............................. 600/219 |
| 7,594,888 B2 * | 9/2009 | Raymond et al. ............. 600/219 |
| 2004/0230191 A1 * | 11/2004 | Frey et al. ........................ 606/57 |
| 2005/0096508 A1 * | 5/2005 | Valentini et al. .............. 600/210 |

(Continued)

*Primary Examiner* — Todd Manahan
*Assistant Examiner* — Eric S. Gibson
(74) *Attorney, Agent, or Firm* — Panitch Schwarze Belisario & Nadel LLP

(57) ABSTRACT

An instrument for spinal surgery for retracting soft tissue and mounting between a superior spinous process and an inferior spinous process includes a relatively rigid frame, a first retractor blade mounted to the frame and a distractor element movably mounted to the frame. The distractor element has a body, a proximal end and a distal end. The distractor element has a thickness and a length. The distractor element is configured for mounting between the superior and inferior spinous processes in a working configuration. The distractor element is generally tapered at the distal end in an insertion configuration. The instrument also includes an insertion shaft attached to the proximal end and a first shaft joint mounted between the frame and the insertion shaft.

9 Claims, 17 Drawing Sheets

(56) References Cited

U.S. PATENT DOCUMENTS

| | | |
|---|---|---|
| 2005/0171403 A1* | 8/2005 | Paolitto et al. ............... 600/205 |
| 2005/0245937 A1* | 11/2005 | Winslow ......................... 606/90 |
| 2006/0142762 A1 | 6/2006 | Michelson |
| 2006/0235279 A1* | 10/2006 | Hawkes et al. ............... 600/222 |
| 2007/0021656 A1 | 1/2007 | Martin et al. |
| 2007/0123753 A1 | 5/2007 | Abdelgany et al. |
| 2007/0185490 A1 | 8/2007 | Implicito |
| 2007/0238932 A1 | 10/2007 | Jones et al. |
| 2008/0071280 A1* | 3/2008 | Winslow ......................... 606/90 |
| 2008/0071380 A1 | 3/2008 | Sweeney |
| 2008/0221394 A1* | 9/2008 | Melkent et al. ............... 600/201 |
| 2008/0300465 A1 | 12/2008 | Feigenwinter et al. |
| 2008/0300686 A1 | 12/2008 | Khoo |
| 2009/0156902 A1* | 6/2009 | Dewey et al. ................. 600/204 |
| 2009/0292316 A1 | 11/2009 | Hess |
| 2010/0010546 A1 | 1/2010 | Hermida Ochoa |
| 2010/0010548 A1 | 1/2010 | Hermida Ochoa |
| 2010/0057130 A1 | 3/2010 | Yue |
| 2010/0106191 A1 | 4/2010 | Yue et al. |
| 2012/0035423 A1* | 2/2012 | Sebastian et al. ............. 600/206 |
| 2012/0078302 A1* | 3/2012 | Reimels ......................... 606/249 |

* cited by examiner

SURGICAL INSTRUMENT SYSTEM AND METHOD FOR PROVIDING RETRACTION AND VERTEBRAL DISTRACTION

CROSS-REFERENCE TO RELATED APPLICATIONS

This application is entitled to priority pursuant to 35 U.S.C. §119 (e) to U.S. Provisional Patent Application No. 61/373,885, filed Aug. 16, 2010, which is incorporated by reference herein in its entirety.

BACKGROUND OF THE INVENTION

Invasive surgical procedures require a surgeon to create an incision in the patient's skin 150 in order to access a surgical site within the patient's body where the surgery is performed. A tissue retractor can be used during the surgical procedure and, in particular, during minimally invasive surgical procedures to temporarily displace tissue and create a relatively small working channel to the surgical site. The working channel of minimally invasive surgical procedures is typically smaller than working channels of traditional open procedures. Such minimally invasive tissue retractors allow unobstructed or nearly unobstructed access to the target or surgical site while limiting the amount of dissection required to achieve exposure of the surgical site. These minimally invasive tissue retractors also typically reduce trauma to the skin 150 and surrounding tissue when compared to traditional open procedures. The retractor can be used, for example, to provide access to a spinal disc, a vertebra and/or vertebrae during spinal surgery.

Referring to FIGS. 1-2B, there are several common lumbar spinal surgical procedures where the patient is positioned in the prone position (FIG. 1) on an operating table 11. A direct posterior lumbar surgical approach to conduct fusion of vertebrae may be referred to as a Posterior Lumbar Interbody Fusion ("PLIF"). An incision for this approach is typically made directly over the patient's mid-line. The procedure is not typically considered a minimally invasive procedure. Soft tissue and muscle are separated and retracted to provide an access channel to the surgical site. In the PLIF approach, soft tissue retraction may be provided by a known manual retractor (Weitlander, Gelpi, Williams, etc.). The procedure may include boney decompression of the lamina and/or facets, removal of the intervertebral disc and preparation of the disc space for fusion. The surgeon often distracts the intervertebral disc so that a relatively large or tall interbody implant or spacer may be inserted between the vertebral bodies, thereby promoting fusion. The surgeon may elect to distract the intervertebral disc space in an effort to restore disc height and sagittal balance. The distraction is often conducted via lamina spreaders, pedicle screw distractors and/or intervertebral body disc spreaders. Subsequently, the interbody spacer may be inserted into the distracted disc space to maintain height while the fusion process occurs over a postoperative timeframe, typically three to nine (3-9) months.

Transforaminal Lumbar Interbody Fusion ("TLIF") is an alternate approach to the PLIF procedure and may generally be conducted in a minimally invasive manner. The surgeon typically makes a single, unilateral surgical incision, approximately two to four centimeters (2-4 cm) lateral to the patient's midline. The approach trajectory is between the multifidus and longissimus muscles 21, 22 using a technique described by Wiltse, which ends at a facet capsule of the targeted vertebral level. The soft tissue and muscle along the surgical path is dissected and retracted to provide a working channel to the surgical site. All surgical work is typically conducted through this single, relatively small incision. Several specialized retractors and systems are available to establish and retain a working channel through the soft tissue. A minimally invasive TLIF approach, with the use of a specialized retraction system, has the potential to be a less traumatic procedure to the patient than the open PLIF procedure, resulting in quicker short-term recovery.

Extracavitary Lumbar Interbody Fusion ("ELIF") is a posterior lumbar interbody fusion technique that approaches the posteriolateral disc from a highly oblique posterior trajectory. The surgeon typically makes a single, unilateral surgical incision about five to eight centimeters (5-8 cm) lateral to the patient's midline with the patient in the prone position (FIG. 1). The trajectory typically approaches the spine 12 between the longissimus and illiocostalis muscles 22, 23 passing through a "safe zone", as described by Kambin (i.e., Kambin's triangle). The ELIF approach is typically considered a minimally invasive technique, similar to the TLIF approach. However, ELIF often presents additional approach challenges over the TLIF procedure.

Prior art retractors are able to create a working channel for the above-described PLIF, ELIF and TLIF procedures. When performing minimally invasive procedures like the TLIF or ELIF procedures, surgical exposure is sometimes limited by the retractor utilized for a procedure and such procedures can be difficult for surgeons to perform through the relatively small surgical channels that are created by such existing retractors. The surgeon typically requires insertion of a plurality of surgical instruments into the working channel to manipulate the surgical site. The surgeon also typically needs to perform secondary manipulative maneuvers of the spine and particular vertebrae, such as distraction or compression. The secondary maneuvers are typically done with separate instruments that may not be insertable through the working channel created by prior art retractors.

When used during a minimally invasive posterior lumbar spine procedure, a tissue retractor is typically inserted through an incision in the skin 150 that can be two to eight centimeters (2-8 cm) lateral from the patient's midline. The retractor is typically stabilized using a table mount arm system that secures the retractor to the operating table 11. The table mount requires additional equipment near the incision and takes-up extra space near the operating table 11. The table mount also requires additional time to set up and properly mount due to the position of the patient 10. The table mount can also clutter the surgical field by obstructing access to the incision. The table mount may also clutter fluoroscopy conducted at the surgical site by blocking and/or obstructing interoperative x-rays or other imaging techniques.

Surgical procedures conducted through a minimally invasive working channel for TLIF and ELIF procedures can be challenging due to space restrictions, confinement and limitations of prior art retractors. Existing retractors may also be limited to specific access angles to the surgical site. TLIF and ELIF procedures can also be complicated by prior art retractors and table mounts "cluttering" the surgical field. Retractor table mount hardware is often cumbersome, requires significant set-up and impedes visibility to the surgical site and through the working channel. Generally, a lateral-type approach incision, typical of ELIF procedures, amplifies the above challenges due to the larger instrument angulations and approach trajectories.

It would be desirable to design and implement a retractor that does not create or minimizes "clutter" in the working field to provide maximum site lines to the surgical site during minimally invasive procedures. It would also be desirable to design and construct a minimally invasive retractor that combines functionality for conducting additional procedures that are typical with ELIF and TLIF procedures, such as distraction of adjacent vertebrae. Further, it would be desirable to design and implement a retractor that is able to define a working channel in various access trajectories that are utilized by the surgeon. The present retractor generally addresses the described disadvantages of prior art retractors.

BRIEF SUMMARY OF THE INVENTION

Briefly stated, a preferred embodiment of the present invention is directed to an instrument for spinal surgery for retracting soft tissue and mounting between a superior spinous process and an inferior spinous process. The instrument includes a relatively rigid frame, a first retractor blade mounted to the frame, a second retractor blade mounted to the frame and a distractor element movably mounted to the frame. The distractor element includes a body, a proximal end and a distal end. The distractor element has a thickness and a length. The distractor element is configured for mounting between the superior and inferior spinous processes in a working configuration. The distractor is generally tapered at the distal end in an insertion configuration. The instrument or retractor also includes an insertion shaft attached to the proximal end and an articulation joint mounted between the frame and the insertion shaft selectively permitting the distractor element to move relative to the frame. The insertion shaft may be comprised of the second retractor blade. The frame and the first and second retractor blades may be integrally formed.

In another aspect, a preferred embodiment of the present invention is directed to a method for providing soft tissue retraction and distraction of superior and inferior vertebrae of a patient's spine utilizing an instrument having a distractor element, a first retractor blade, a second retractor blade, and a frame. The method includes the steps of targeting a surgical site in the lumbar region of the patient's spine, making an incision through the patient's soft tissue to the surgical site, thereby defining a working channel from the patient's skin 150 to the surgical site, inserting the first and second retractor blades into the working channel such that the distal ends of the first and second retractor blades are positioned near the surgical site, inserting the distractor element through the working channel and into a position between a superior spinous process associated with the superior vertebra and an inferior spinous process associated with the inferior vertebra, mounting the distractor element to the frame, and manipulating the first and second retractor blades to expand the working channel. The ordering of the steps in this procedure is not limiting and may be performed in various sequences without departing from the spirit and scope of the present application.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustration, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
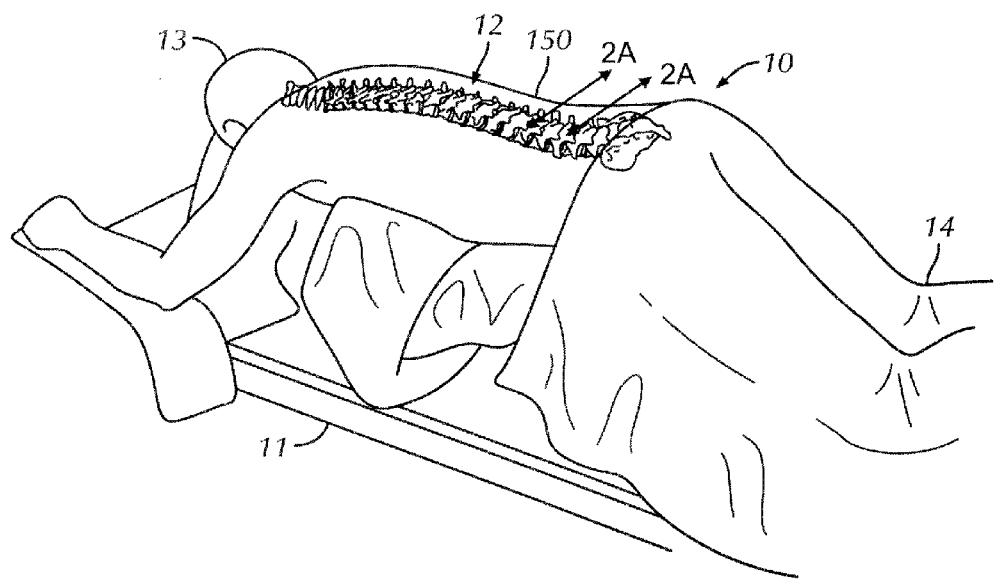
FIG. 1 is a side perspective view of a patient positioned on an operating table in a prone position.

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the geometric center or orientation of the surgical instrument, implants and/or related parts thereof. The words, "anterior," "posterior," "superior," "inferior," "lateral," "medial," "cranial," "cephalad," "caudal," "caudad" and related words and/or phrases designate preferred positions and orientations in the human body or the patient to which reference is made and are not meant to be limiting. The terminology includes the above-listed words, derivatives thereof and words of similar import.

Figure 2A:
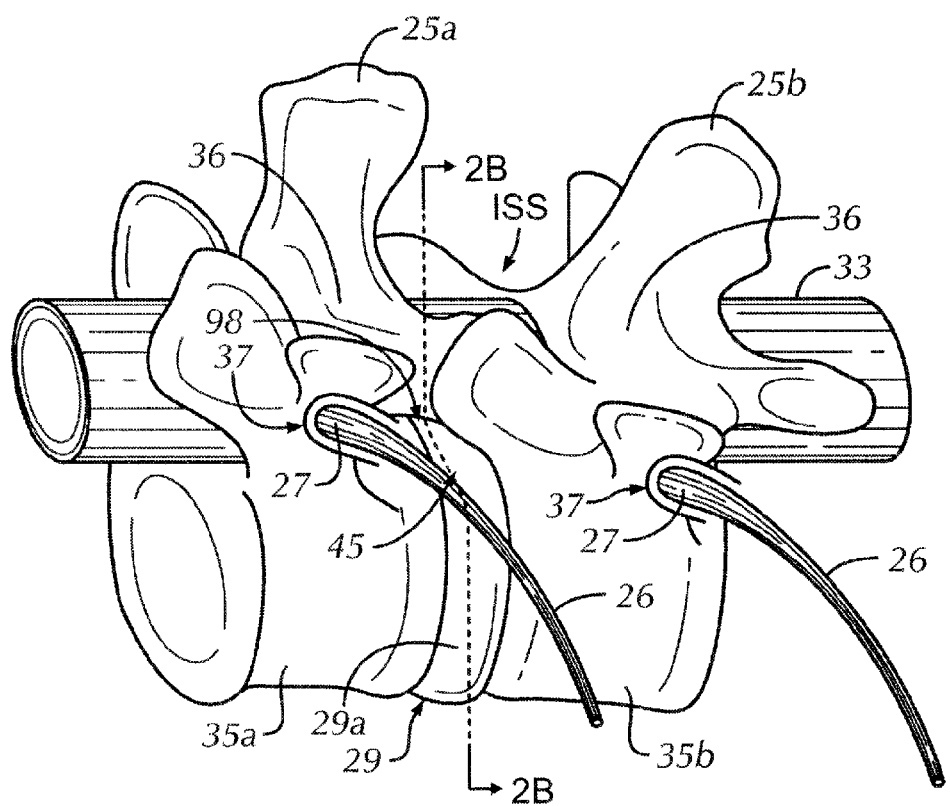
FIG. 2A is a lateral or side perspective view of a lumbar level of the patient's spine taken from the viewpoint of line 2A-2A of FIG. 1.
Figure 2B:
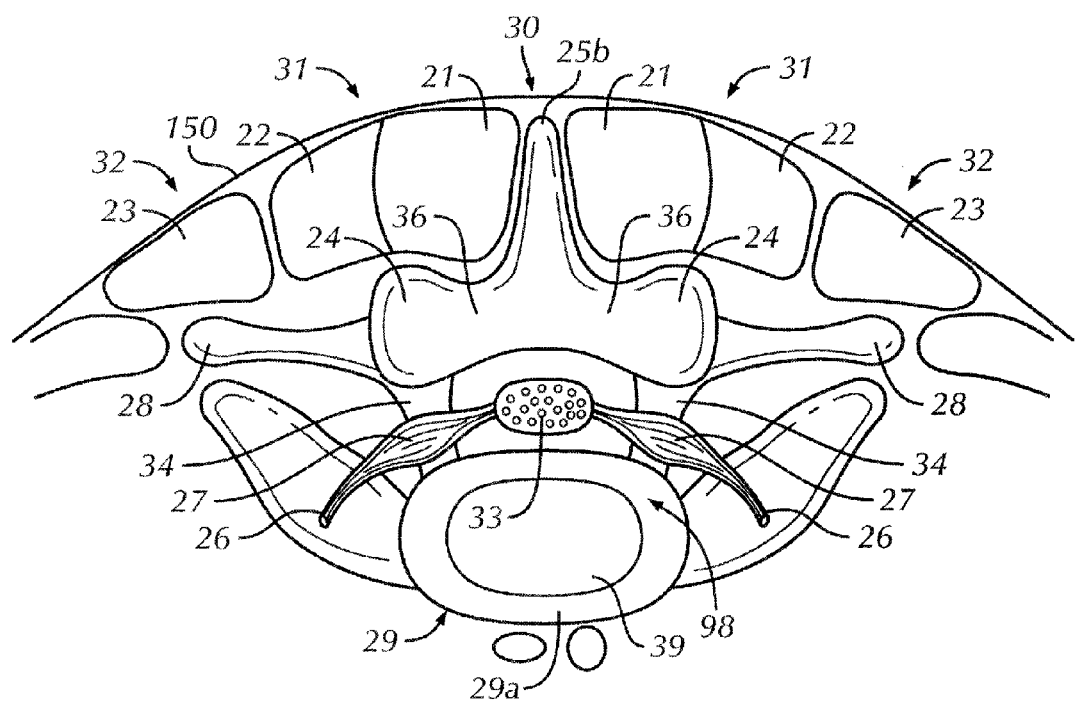
FIG. 2B is a cross-sectional view of a lumbar level of the patient's spine taken along line 2B-2B of FIG. 2A.
Figure 3A:
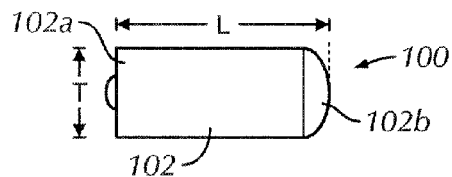
FIG. 3A is a side elevational view of a distraction element of the surgical instrument of FIG. 3.
Figure 3:
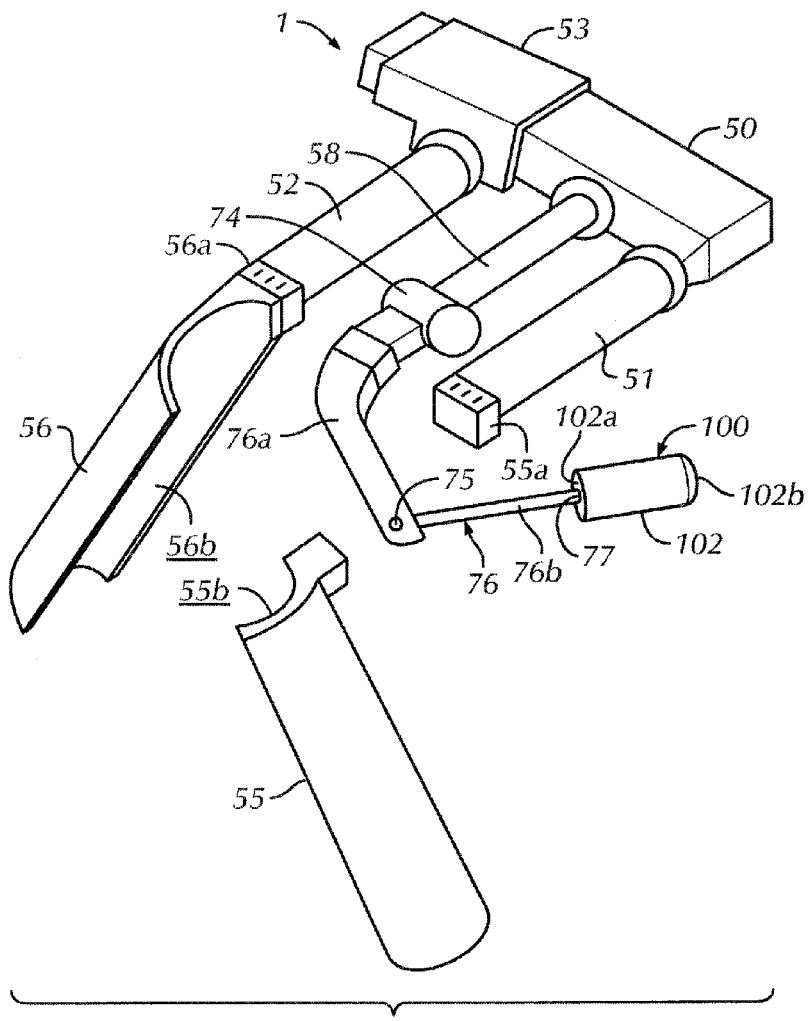
FIG. 3 is a front perspective view of a surgical instrument in accordance with a first preferred embodiment of the present invention.

Referring to FIGS. 1-3, preferred embodiments of the present invention are directed to an instrument 1 for spinal surgery for retracting soft tissue and mounting between a superior spinous process 25a and an inferior spinous process 25b in an interspinous space ISS. In surgeries utilizing the preferred instrument 1, a patient 10 is typically positioned in the chest down or prone position (FIG. 1) on the operating or surgical table 11. In the chest down or prone position, the patient's head 13 is positioned at one end of the table 11 and their legs 14 are positioned at an opposite end of the table 11. The chest down or prone position provides the surgeon with relatively easy access to the patient's spine 12. The direction toward the patient's head 13 is typically referred to as the cranial or cephalad direction and the direction towards the patient's legs 14 is typically referred to as the caudal or caudad direction.

Referring to FIGS. 1-3 and 13, a typical surgical site 98 targeted for spinal surgeries utilizing the preferred instrument 1 is a lumbar intervertebral disc 29 positioned between a superior vertebral body 35a and an inferior vertebral body 35b. The patient's spinal cord 33 traverses the cervical and thoracic regions of the spine 12 and generally transitions in the upper lumbar region of the spine 12 into the cauda equina for the remainder of its length. For convenience, the spinal cord 33 is utilized generically herein to include the spinal cord 33 in the cervical and thoracic regions, as well as the cauda equina. The preferred embodiments of the instrument 1 are not limited to use in any particularly region of the spine 12 and may be adapted for use in any region of the spine 12, despite the depiction and description herein focusing generally on the lumbar region of the spine 12. The patient's spine 12 is shaped to create a boney ring around the patient's spinal cord 33 to protect the spinal cord 33 and support the patient's body. The boney portion at the anterior side of the spine 12 is comprised of the vertebral bodies 35a, 35b and pedicles 34 extend from the bodies 35a, 35b along a side or each side of the spinal cord 33 to surround and protect the sides of the spinal cord 33. The posterior vertebral arch includes the pedicles 34, the spinous process 25a, 25b, lamina 36 extending from the spinous process 25a, 25b and facets 24 located between the pedicles 34 and transverse processes 28. The facets 24 are associated with synovial joints that aid in load transfer and control motion at elements of the patient's spine 12. The spinous processes 25a, 25b are boney protrusions that extend generally in a posterior direction and can be felt as a series of bumps along the center or mid-line of the patient's back. On each side of the spinous processes 25a, 25b, lateral to the facets 24, are transverse processes 28.

Positioned between each of the superior and inferior vertebral bodies 35a, 35b is an intervertebral disc 29 that functions as a shock absorber in the spine 12. The disc 29 assists the facets 24 in controlling load and motion of the spine 12. Each disc 29 has an outer annulus fibrosus 29a and a nucleus pulposus 39. The nucleus 39 of the disc 29 has a relatively high water content, which helps maintain height, flexibility and load-carrying capability of the disc 29.

Nerve roots 26 extend from the spinal cord 33 through the boney structure of the spine 12. The nerve roots 26 initiate from the spinal cord 33, traverse through a neural foramen 37 between the vertebrae of the spine 12 and pass into the muscle groups lateral of the spine 12. A slightly larger section of the nerve root 26 proximate the exit of the neural foramen 37 is referred to as a root ganglion 27. The root ganglion 27 is a relatively sensitive section of the nerve root 26 and is typically approached with particular care during surgery.

The erector spinae muscles are located at the posterior of the patient adjacent the lumbar region of the spine 12. The erector spinae muscles include a multifidus muscle 21 that is positioned adjacent the spinous processes 25a, 25b, the longissimus muscles 22 that are positioned lateral relative to the multifidus muscles 21 and the illiocostalis muscles 23. Potential dissection planes lie between these muscles 21, 22, 23 and are utilized by surgeons to gain access to a surgical site 98 of the patient's spine 12. The multifidus muscles 21 are positioned and attached to the spinous processes 25a, 25b and the posterior elements of the vertebral arch to each facet 24.

A PLIF surgical approach trajectory 30 typically begins with an incision over the spinous processes 25a in the skin 150 of the patient 10 along the mid-line of the spine 12 over a target level of the spine 12. The multifidus muscles 21 on either side of the spinous processes 25a, 25b are released from their attachments and retracted laterally to expose a portion of the posterior spine 12.

A TLIF surgical approach trajectory 31, typically begins two to four centimeters (2-4 cm) lateral of a midline of the patient's spine 12. The TLIF trajectory 31 is typically angled at approximately fifteen to thirty degrees (15-30° from vertical when the patient 12 is in the prone position (FIG. 1). Generally, the Wiltse muscle-splitting approach is utilized. The surgeon typically dissects through fascia layers and parts the multifidus and longissimus muscles 21, 22. This approach typically terminates through the soft tissue at the facets 24.

In an ELIF surgical approach trajectory 32, and incision is typically made in the patient's skin 150 approximately five to eight centimeters (5-8 cm) lateral of the midline. The ELIF trajectory 32 is typically approximately forty-five to sixty degrees (45-60° from vertical when the patient 10 is in the prone position. The trajectory is generally established fluoroscopically by approximating a discogram view. The surgeon dissects through the fascia layers and separates the longissimus and illiocostalis muscles 22, 23. This ELIF trajectory 32 generally terminates lateral of the facets 24 near a tip or mid-span of the transverse processes 28.

Referring to FIGS. 2A and 2B, a disc 29 may be accessed through Kambin's triangle utilizing the ELIF approach trajectory 32. Kambin's triangle is typically defined or bounded by the nerve root 26, the superior border of the inferior body 35b and the traversing nerve root.

Figure 11A:
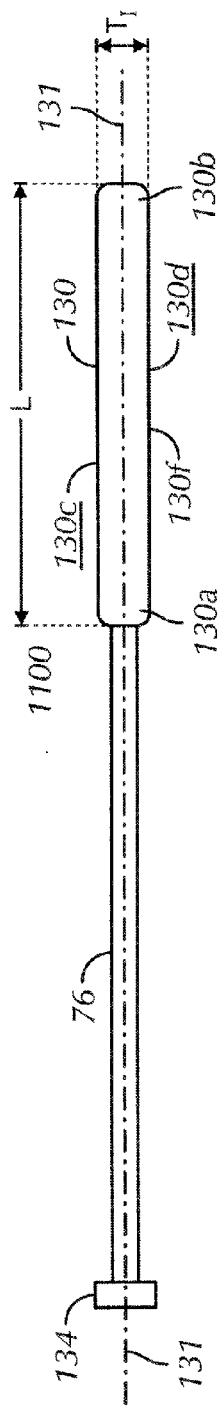
FIG. 11A is a right-side elevational view of a distractor element and insertion shaft in accordance with a sixth preferred embodiment of the present invention.
Figure 11B:
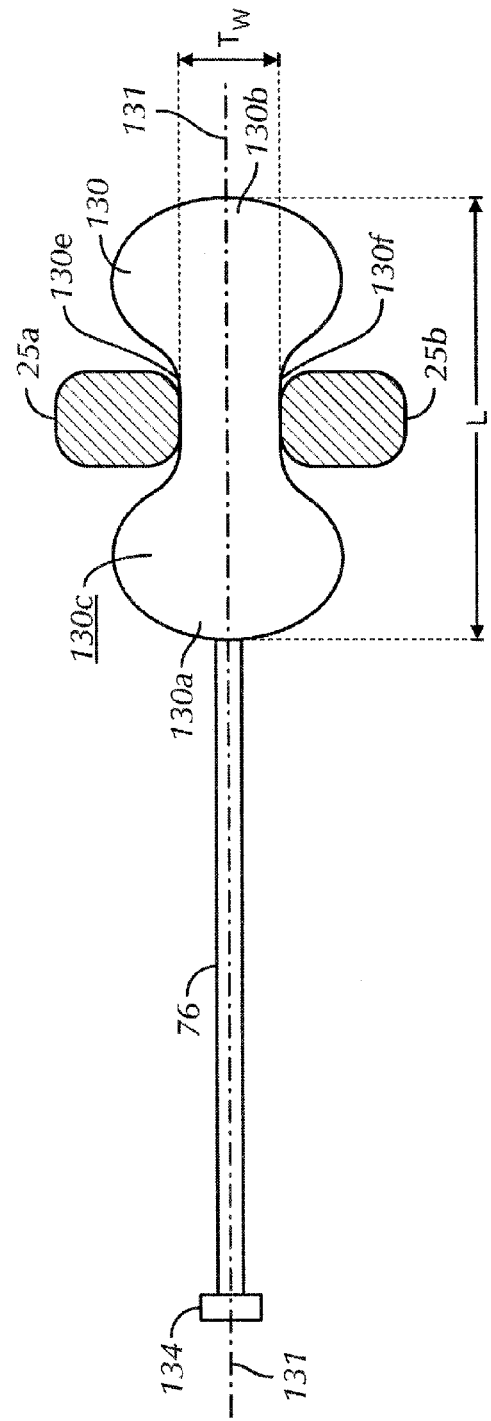
FIG. 11B is a top plan view of the distractor element and insertion shaft of FIG. 11A.
Figure 12:
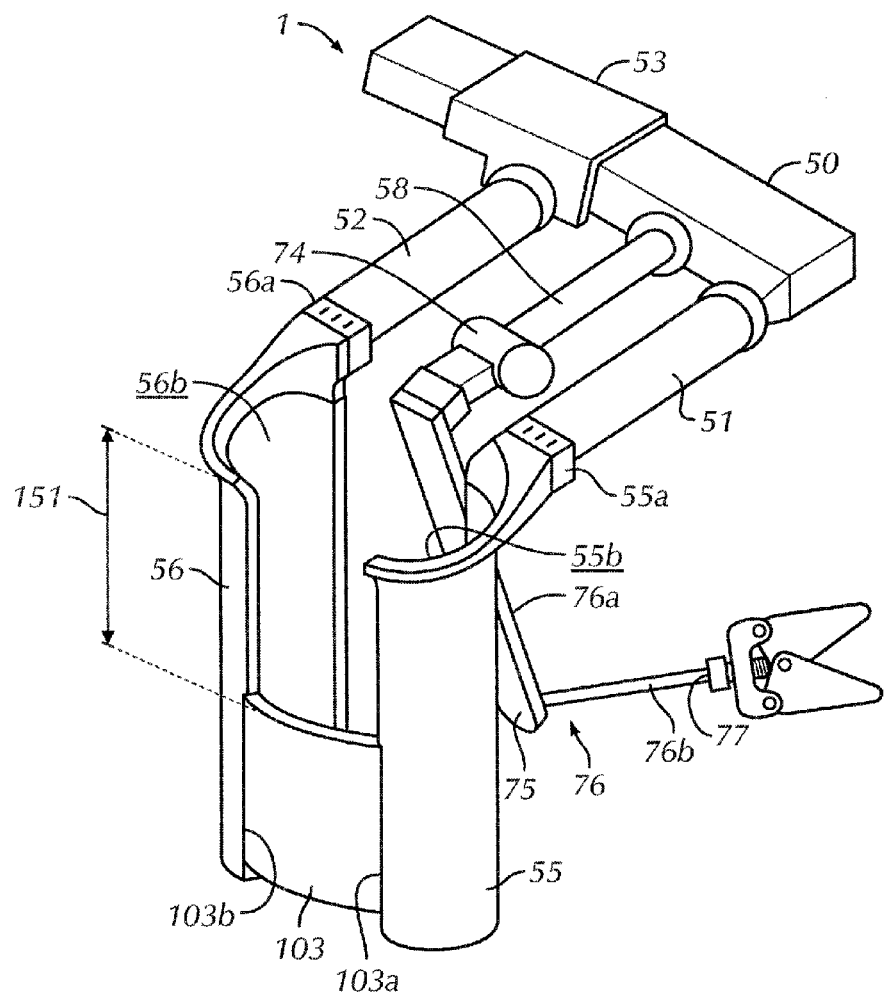
FIG. 12 is a front perspective view of a surgical instrument in accordance with the second preferred embodiment of the present invention.

Referring to FIGS. 3 and 12, the preferred embodiments of the present invention are directed to the instrument 1 for spinal surgery for retracting soft tissue and mounting between the superior and inferior spinous processes 25a, 25b. Referring to FIGS. 3-12, the instruments 1 of the first, second, third, fourth, fifth and sixth preferred embodiments are able to retract soft tissue, such as the erector spinae muscles, including the multifidus muscles 21, longissimus muscles 22, illiocostalis muscles 23, skin 150, nerves, blood vessels and other soft tissue to define a working channel 63 between the patient's skin 150 and a surgical site 98.

The preferred instruments 1 include a relatively rigid frame 50, a first retractor blade 55 mounted to the frame 50 and a second retractor blade 56 movably mounted to the frame 50. The second retractor blade 56 may be comprised of an insertion shaft 76, as will be described in greater detail below. The frame 50 may be relatively straight, as shown, or may have an alternative shape, such as curved, circular, arcuate or nearly any other shape that is desirable to a surgeon and/or designer. The first and second blades 55, 56 are preferably constructed of a biocompatible material such as stainless steel, coated aluminum, titanium, PEEK or other biocompatible metals, polymers and/or combinations of these materials. The blades 55, 56 preferably have a length sufficient to extend from the opening of the working channel 63 at the patient's skin 150 to the surgical site 98. However, the blades 55, 56 are preferably not significantly longer such that clutter at the opening of the working channel 63 is limited during use.

Referring to FIGS. 1, 3, 12 and 13, in the preferred embodiments, the first blade 55 is preferably a caudal blade 55 and the second blade 56 is preferably a cranial blade 56. The caudal or first blade 55 is preferably connected to the frame 50 by a static arm 51 that extends from the frame 50, generally perpendicularly. The first blade 55 is preferably removably mountable to the static arm 51 at a first blade attachment joint 55a. The first blade 55 is removably mountable such that a plurality of blades 55 having variable lengths (not shown) may be mounted to the static arm 51 at the first blade attachment joint 55a to accommodate variable length working channels 56 depending upon the patient 10 and/or surgeon preference. The static arm 51 preferably extends a relatively short distance from the frame 50, to distance the frame 50 from the opening of the working channel 63 and limit clutter at the opening of the working channel 63. The static arm 51 is not limited to being fixed or statically secured to the frame 50 and may be movable relative to the frame 50. The first and second blades 55, 56 are not limited to being removably mounted to the frame 50 at the attachment joints 55a, 56a, as shown in the preferred embodiments. For example, the attachment joints 55a, 56a may be comprised of attachment blades or holder blades that are configured to retract soft tissue and movably and/or removably accept the first and second blades 55, 56. Such a configuration could permit the first and second blades 55, 56 to slide longitudinally within the holder blades/attachment joints 55a, 56a so that a surgeon is able to effectively modify the length of the blades or depth of the blades 55, 56.

The second or cranial blade 56 is preferably constructed of the same or similar materials as the first blade 55 and is preferably mounted to the frame 50 by a sliding arm 52 and a slider 53. The slider 53, sliding arm 52 and second or cranial blade 56 are preferably slidably and removably mounted to the retractor frame 50 such that the first and second blades 55, 56 may be moved relative to each other during use to expand or contract the working channel 63. The first and second blades 55, 56, static arm 51, sliding arm 52, slider 53 and frame 50 are each preferably constructed of a relatively rigid, strong, biocompatible material that is able to take on the general shape of these components and withstand the normal operating conditions of these components. The components may be constructed of radiolucent or partially radiolucent materials to limit visual obstruction of x-rays, fluoroscopy and/or other imaging techniques.

The second blade 56 is preferably removably mountable to the sliding arm 52 at a second blade attachment joint 56a similar to the first blade attachment joint 55a. The first and second blade attachment joints 55a, 56a may be constructed of nearly any structure or element that permits removable attachment of the first and second blades 55, 56 to the static and sliding arms 51, 52, respectively. The first and second attachment joints 55a, 56a preferably at least partially secure or lock the blades 55, 56 to the static and sliding arms 51, 52 by a securing mechanism, such as a force fit, pinning, cover plate, screw clamp, ratchet mechanism, hook and loop material, adhesives, snap-fit or other releasably securable mechanism that releasably secures the first and second blades 55, 56 to the static and sliding arms 51, 52.

The slider 53 is preferably slidably mounted to the frame 50 such that the slider 53 and, thereby, the sliding arm 52 and second blade 56 when mounted thereon, are movable relative to the frame 50, static arm 51 and first blade 55. The slider 53 is preferably slidable along the length of the frame 50 and may be locked in various positions along the frame 50 by a locking mechanism, such as a rack-and-pinion gear, pawl ratchet, friction clamp, screw, pin, snap lock, hook and loop material or other selectively lockable mechanism that is able to selectively secure the slider 53, sliding arm 52 and second blade 56 in position relative to the frame 50. In addition, the static arm 51 is not limited to being fixed to the frame 50 and may be configured to move relative to the frame 50 utilizing a similar structure as the sliding arm 52. Further, the preferred instruments 1 are not limited to inclusion of the slider 53 to facilitate movement of the sliding arm 52 and/or second blade 56 and the sliding arm 52 and second blade 56 may be movable relative to the frame 50 using numerous mechanisms that permit movement of these components relative to the frame 50, such as bearings, pins, rotating mechanisms, sliding mechanisms and like mechanisms.

The first and second blades 55, 56 preferably include inner surfaces 55b, 56b that are curved or arcuate and at least partially define the working channel 63. In the preferred embodiments, the inner surfaces 55b, 56b have a generally half-circle or partial half-circle cross-section, thereby defining a circular or oblong working channel 63 if the blades 55, 56 are positioned in facing engagement with the inner surfaces 55b, 56b facing each other. The inner surfaces 55b, 56b are not limited to having half-circular shapes and may be constructed to have nearly any shape or configuration for defining the working channel 63 such as oblong, triangular, oval or nearly any size, shape or configuration that would be desirable to a user or surgeon. Preferably, the first and second blades 55, 56 have a relatively low profile or size for insertion into the patient's 10 body and subsequent expansion of the working channel 63 by manipulating the slider 53 or the blades 55, 56 themselves relative to the arms 51, 52 to expand the working channel 63 and provide an optimum line of site or working channel 63 for the surgeon to best visualize the surgical site 98.

Referring to FIGS. 3, 11 and 12, the surgical instruments 1 of the preferred embodiments may also include a third retractor blade 103 mounted to the frame 50. The third retractor blade 103 may be constructed of a relatively flexible material and mounted between the first and second retractor blades 55, 56. The third retractor blade 103 may be mounted to the first retractor blade 55 at a first flexible blade attachment joint 103a and to the second retractor blade 56 at a second flexible blade attachment joint 103b. The flexible blade 103 may be fixed at the first and second flexible blade attachment joints 103a, 103b on the first and second blades 55, 56 or may be removably mountable to the first and second blades 55, 56 at the first and second flexible blade attachment joints 103a, 103b. The flexible third retractor blade 103b may be constructed of nearly any biocompatible, flexible material that is able to take on the general size and shape of the third flexible blade 103 and withstand the normal operating conditions of the third flexible blade 103. In a closed position of the instruments 1 of the preferred embodiments, wherein the first and second blades 55, 56 are positioned adjacent to each other with their inner surfaces 55b, 56b facing each other, the third flexible blade 103 is preferably positioned within the working channel 63. When the instrument 1 is moved from the closed position to an open or expanded position, the flexible blade 103 stretches as the first and second blades 55, 56 move away from each other. The third or flexible blade 103 provides an additional impediment to soft tissue flexing into or impeding the working channel 63, thereby providing an expanded line of site or working channel 63 for the surgeon and improved visibility of the surgical site 98.

The flexible or third blade 103 may be attached at a third blade distance 151 measured from the patient's skin level 150 or a top of the first and second blades 55, 56. This subcutaneous positioning of the third or flexible blade 103 allows clearance when the surgeon is moving surgical instruments 1 in a highly oblique trajectory, as will be described in greater detail below. The third or flexible blade 103 is not limited to being secured to the first and second blades 55, 56 at the third blade distance 151 below the patient's skin level 150 or from the top of the first or second blades 55, 56 and may extend along the entire length of the first and second blades 55, 56, from a position near the top of the first and second blades 55, 56 to a position that does not extend to the tips of the first and second blades 55, 56 or may be otherwise positioned relative to the first and second blades 55, 56 based on preferences.

The third blade 103 is not limited to constructions as a flexible blade and may be comprised of a relatively rigid blade (not shown) similar to the first and second blades 55, 56. For example, the third blade 103 may be constructed of a rigid blade that is mounted to the frame 50 by an additional arm extending generally perpendicularly from the frame 50 or may be comprised of multiple additional blades mounted to the frame 50 to assist in defining the working channel 63. In addition, the flexible or third blade 103 may be slidably mounted to the first and second retractor blades 55, 56 at the first and second flexible blade attachments 103a, 103b such that the flexible blade 103 may be positioned at different depths along the first and second blades 55, 56 based upon surgeon preference. The third blade 103 may further be comprised of a relatively rigid blade that attaches to the a static bar 58, which will be described in greater detail below, to provide retraction in a generally lateral direction during use. The third blade 103 may also incorporate a nerve root retractor (not shown) for retracting the nerve root 26 or root ganglion 27.

Referring to FIGS. 3-15, the instruments 1 of the preferred embodiments also include a distractor element 100, 80, 90, 110, 120, 130 that is movably mounted to the frame 50. The distractor element 100, 80, 90, 110, 120, 130 may have various configurations that are adapted for mounting between the superior and inferior spinous processes 25a, 25b to secure the preferred instruments 1 to the patient 10. Securing the preferred instruments 1 to the patient 10 via the preferred distractor elements 100, 80, 90, 110, 120 generally eliminates the necessity for table mounted retractors that are typical for the use of retractor blades and permits the preferred instruments 1 to move with the patient 10, if the patient 10 moves during surgery. In contrast, table mounted retractors of the prior art are typically ill-equipped to accommodate movements of the patient 10 relative to the table 11 during surgical procedures.

The various preferred embodiments of the distractor element 100, 80, 90, 110, 120, 130 preferably include a first preferred distractor element 100, a second preferred, hinged distractor element 80, a third preferred, screw-type distractor element 90, a fourth preferred, compression-type distractor element 110, a fifth preferred, balloon-type distractor element 120 and a sixth preferred, flattened distractor element 130. The preferred distractor elements 100, 80, 90, 110, 120, 130 are not limited to the first through sixth preferred distractor elements 100, 80, 90, 110, 120, 130 and may have various additional configurations for mounting between the superior and inferior spinous processes 25a, 25b, for example, the distractor element 100, 80, 90, 110, 120, 130 may be comprised of a H-shaped element with pivoting legs resulting in a relatively minimal profile for insertion into the patient's body and between the superior and inferior spinous processes 25a, 25b, but may be expanded for mounting between the spinous processes 25a, 25b with inner surfaces of the H-shape contacting or proximate sides of the spinous processes 25a, 25b to secure the H-shaped element to the spinous processes 25a, 25b and the patient 10. Alternative configurations of the preferred distractor elements 100, 80, 90, 110, 120, 130 are preferably able to be positioned between the superior and inferior spinous processes 25a, 25b, be secured to the frame 50 and secure the instruments 1 to the patient 10.

Figure 13:
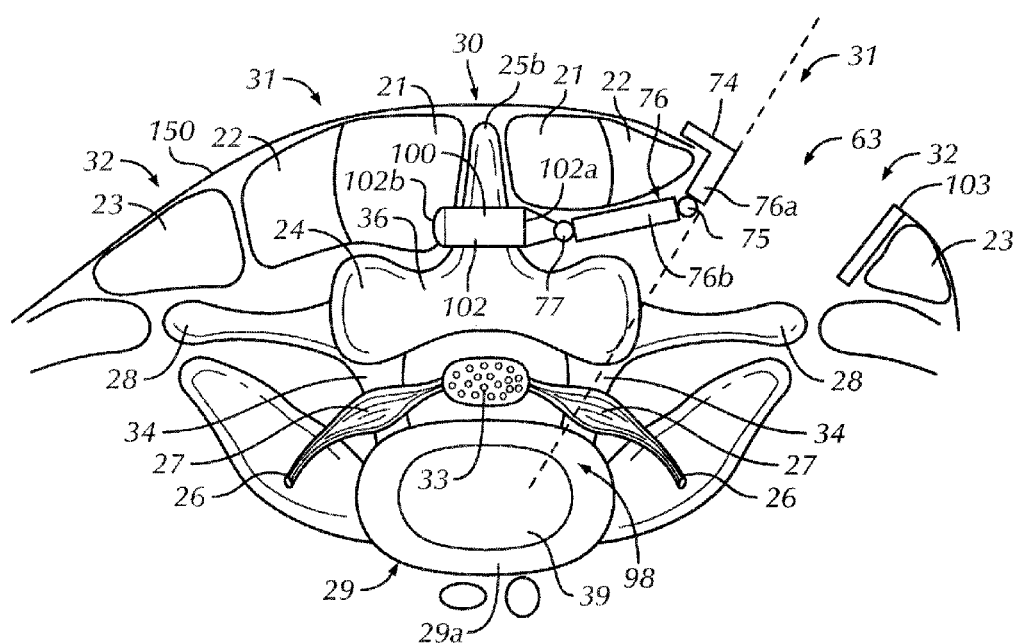
FIGS. 13-15 are cross-sectional views of the lumbar level in the patient's spine taken along line 2B-2B of FIG. 2A with the surgical instrument of the first preferred embodiment of the present invention mounted to a lumbar level of the patient's spine and showing various steps of an interbody fusion procedure.

Referring to FIGS. 2A, 3A and 13, the first preferred distractor element 100 has a body 102, a proximal end 102a and distal end 102b. The distractor element 102 of the first preferred embodiment is configured for mounting between the superior and inferior spinous processes 25a, 25b in a working configuration (FIG. 13) such that the distal end 102b is located at one side of the spinous processes 25a, 25b and the proximal end 102a is positioned at an opposite side of the spinous processes 25a, 25b. The distractor element 100 preferably has a thickness T and a length L. The distractor element 100 of the first preferred embodiment is generally tapered at the distal end 102b. The distractor element 100 may be arcuately, linearly or otherwise tapered to promote insertion of the distractor element 100 between the spinous processes 25a, 25b into the interspinous space ISS. The distal end 102b of the distractor 100 has a tapered nose to facilitate insertion through the soft tissue between the superior and inferior vertebrae 25a, 25b. The nose or distal end 102b may be pointed, bullet-shaped or otherwise configured for urging through the soft tissue between the superior and inferior spinous processes 25a, 25b during use, as is described in greater detail below.

Referring to FIGS. 3, 3A and 12-15, in the first preferred embodiment, the distractor element 100 has a generally cylindrical body 102 with the tapered nose or distal end 102b and a relatively consistent length L and thickness T. A plurality of distractors 100 (not shown) of the first preferred embodiment are preferably provided to the surgeon having various lengths L and thicknesses T for selection by the surgeon depending upon the size of the patient 10, the size of the interspinous space ISS, or other factors. Accordingly, the distractor element 100 of the first preferred embodiment is preferably removably mountable to the frame 50 such that the surgeon can select the appropriately sized distractor element 100. Preferably, the first distractor element 100 is removably mountable from the frame 50 at an distractor attachment joint 77, which will be described in greater detail below. Alternatively, the first preferred distractor element 100 may be secured directly to a malleable insertion shaft 76 that may be manipulated by a surgeon once the distractor element 100 is mounted in the interspinous space ISS to retract soft tissue and/or orient the distractor element 100 and insertion shaft 76 relative to the frame 50 for mounting thereto.

Figure 4:
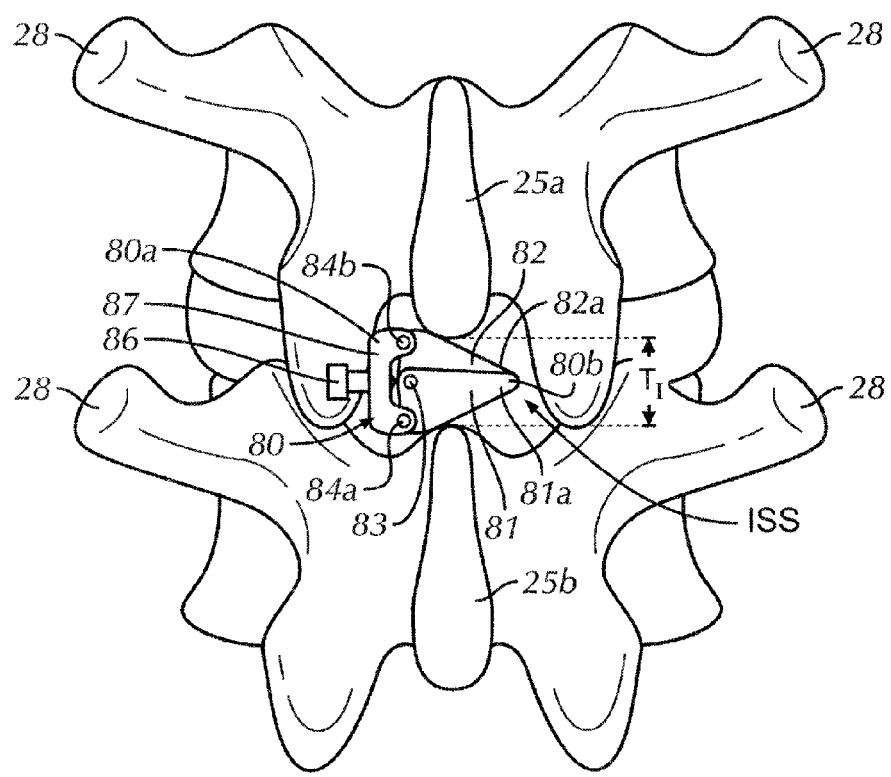
FIG. 4 is a side elevational view of a distractor element in accordance with a second preferred embodiment of the present invention, shown in an insertion configuration from a posterior view of the patient's spine.
Figure 5:
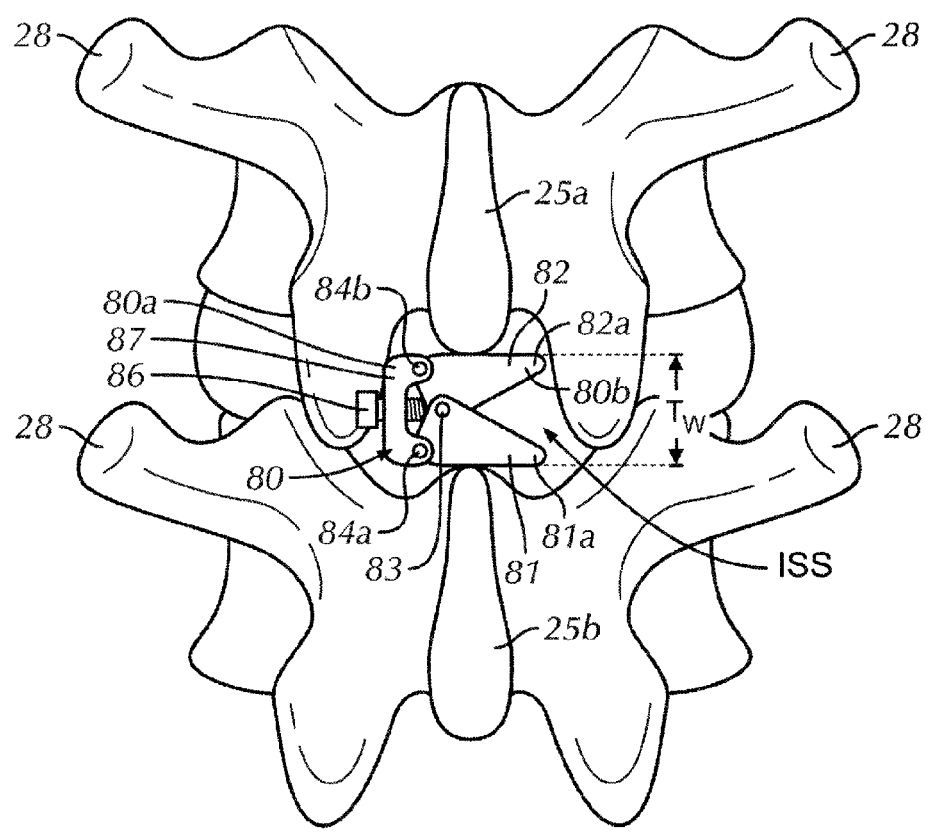
FIG. 5 is a side elevational view of the distractor element of FIG. 4, shown in a working configuration from a posterior view of the patient's spine.

Referring to FIGS. 4 and 5, in a second preferred embodiment, the distractor element 80 includes a distractor frame 87, a first distractor blade 81 having a first distractor tip 81a, a second distractor blade 82 having a second distractor tip 82a and a blade pivot joint 83. The first distractor blade 81 is pivotable relative to the second distractor blade 82 and the blade pivot joint 83. The first and second distractor tips 81a, 82a are preferably positioned adjacent each other in an insertion configuration (FIG. 4) and are spaced from each other in the working configuration (FIG. 5). The distractor element 80 of the second preferred embodiment is expandable such that its working thickness $T_W$ is greater in the working configuration than its insertion thickness $T_I$ in the insertion configuration. Referring specifically to FIG. 4, in the insertion configuration, the thickness T is measured generally along a midlength of the first and second distractor blades 81, 82 where the distractor 80 is expected to be positioned between the superior and inferior spinous processes 25a, 25b. In the insertion configuration, the distractor element 80 has an insertion configuration thickness $T_1$. Referring specifically to FIG. 5, the first and second distractor blades 81, 82 are pivoted relative to each other to expand the blades 81, 82, distract the interspinous space ISS, and secure the instrument 1 to the patient's spine 12. In this working position, the distractor 80 has a working thickness $T_W$ that is greater than the insertion thickness $T_1$.

The distractor element 80 of the second preferred embodiment preferably includes a pin at the blade pivot joint 83 to permit the pivotable movement between the first and second distractor blades 81, 82. The first and second distractor blades 81, 82 are also preferably pinned to the frame 87 at first and second distractor blade pivots 84a, 84b. A rotatable screw 86 is preferably threaded into a proximal end of the frame 87 and pushes on the pin associated with the distractor blade pivot joint 83. Tightening or urging of the rotatable screw 86 toward the first and second distractor blade tips 81a, 82a causes the distractor blade tips 81a, 82a to move away from each other and, if the distractor element 80 is in the insertion configuration, to move toward the working configuration. The rotatable screw 86 is tightened until the first and second distractor blades 81, 82 create the desired distraction of the interspinous space ISS and the instrument 1 is securely mounted to the patient's spine 12. The distractor element 80 of the second preferred embodiment may also include an oblong hole (not shown) in the first and second distractor blades 81, 82 at the distractor blade pivot joint 83 to accommodate the pivotable movement of the first and second distractor blades 81, 82 relative to each other.

Figure 6:
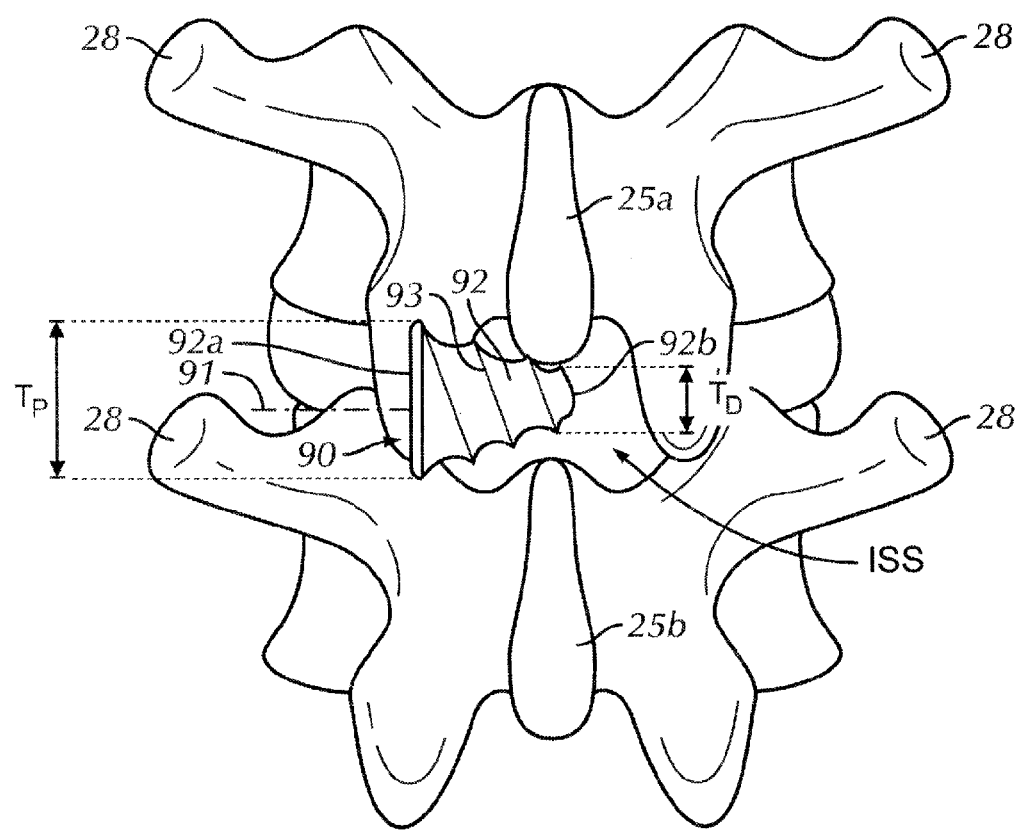
FIG. 6 is a side elevational view of a distractor element in accordance with a third preferred embodiment of the present invention, shown being inserted between superior and inferior spinous processes from a posterior view of the patient's spine.
Figure 7:
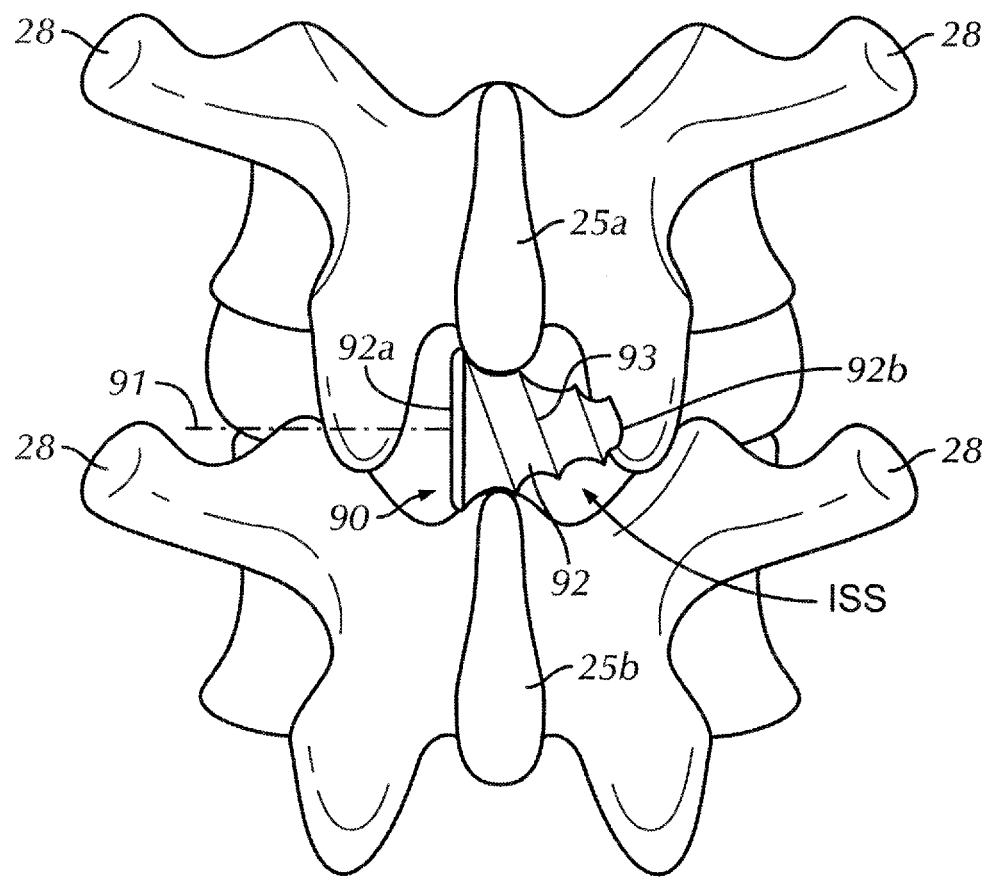
FIG. 7 is a side elevational view of the distractor element of FIG. 6, shown in engagement with the superior and inferior spinous processes from a posterior view of the patient's spine.

Referring to FIGS. 6 and 7, a distractor element 90 in accordance with a third preferred embodiment of the instrument 1 includes threads 93 on a body 92 that are configured to facilitate insertion of the distractor element 90 between the superior and inferior spinous processes 25a, 25b. The thickness of the distractor element 90 of the third preferred embodiment includes a distal thickness $T_D$ near a distal end 92b and a proximal thickness $T_P$ near the proximal end 92a. The distal thickness $T_D$ is less than the proximal thickness $T_P$. The body 92 preferably tapers from the proximal end 92a having the proximal thickness $T_P$ toward the distal end 92b having the distal thickness $T_D$ and generally includes the threads 93 on nearly the entire length of the body 92. Accordingly, the distractor element 90 of the third preferred embodiment may be screwed into the interspinous space ISS between the superior and inferior spinous processes 25a, 25b. The distractor element 90 of the third preferred embodiment is preferably inserted into the interspinous space ISS along a longitudinal axis 91 of the distractor element 90. Specifically, the distractor element 90 is preferably rotated about the axis 91, thereby allowing the threads 93 to engage the superior and inferior spinous processes 25a, 25b to secure the distractor element 90 to the superior and inferior spinous processes 25a, 25b. The distractor element 90 may likewise be rotated in an opposite direction about the longitudinal axis 91 to urge the distractor element 90 out of engagement with the superior and inferior spinous processes 25a, 25b if the instrument 1 and/or distractor element 90 is being removed from the working channel 63 or it is desirable to rearrange the distractor element 90 in the interspinous space ISS.

Figure 8:
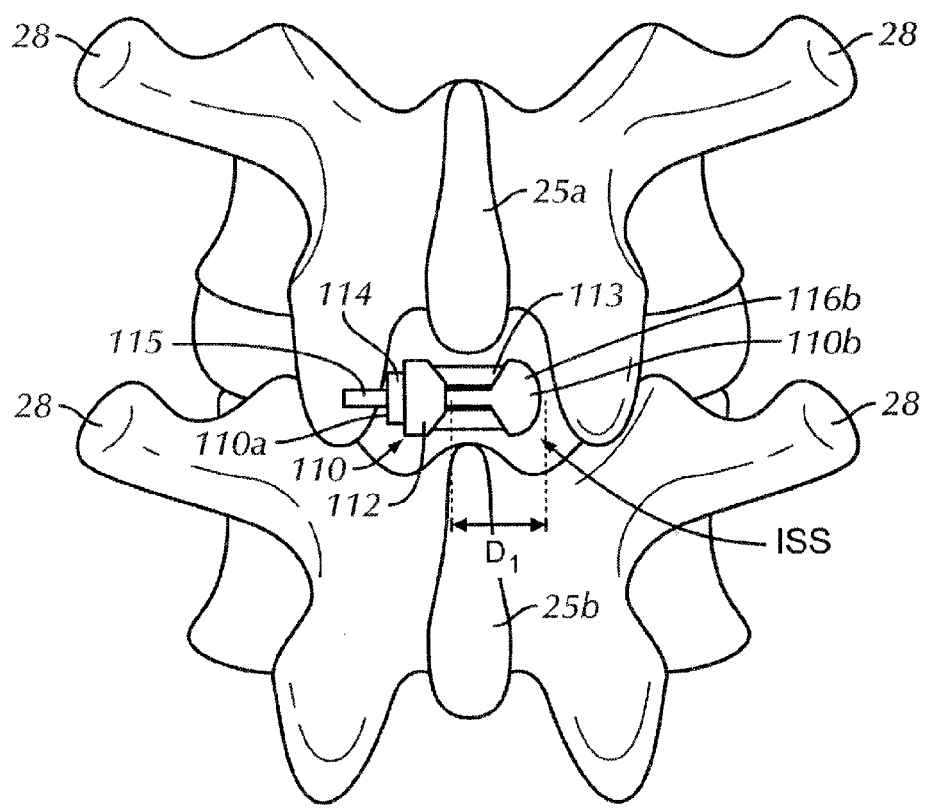
FIG. 8 is a side elevational view of a distractor element in accordance with a fourth preferred embodiment of the present invention, shown in an insertion configuration from a posterior view of the patient's spine.
Figure 9:
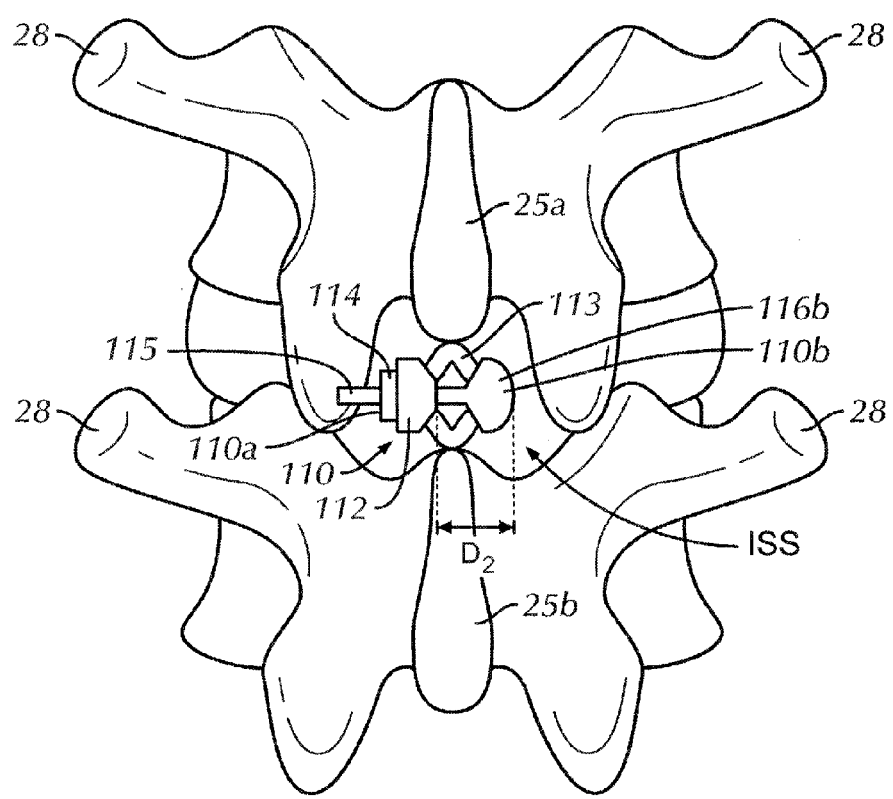
FIG. 9 is a side elevational view of the distractor element of FIG. 8, shown in a working configuration from a posterior view of the patient's spine.

Referring to FIGS. 8 and 9, in a fourth preferred embodiment, a distractor element 110 includes a deformable element 113, a distractor support shaft 115, a slider element 112 movably mounted to the distractor shaft 115 and a lock element 114. The slider element 112 is movable relative to the distractor support shaft 115 to articulate the distractor element 110 between the insertion configuration (FIG. 8) and the working configuration (FIG. 9). The slider element 112 preferably applies a compression forced to the deformable element 113 to urge the deformable element 113 from the insertion configuration to the working configuration. The deformable element 113 is also preferably at least partially deformable around portions of the superior and inferior spinous processes 25a, 25b to secure the instrument 1 to the patient 10 and the patient's spine 12.

In the fourth preferred embodiment, the slider element 112 is arranged at a first distance $D_1$ from a distal end 116b of the distractor element 110 in the insertion configuration and at a second distance $D_2$ from the distal end 116b in the working configuration. The second distance $D_2$ is less than the first distance $D_1$. The slider 112 is preferably movable and lockable at various positions along the distractor support shaft 115 through the use of a nut, which is the locking element 114 in the fourth preferred embodiment. The nut 114 is movably secured to the distractor support shaft 115 by a threaded engagement in the fourth preferred embodiment. The nut 114 is movable along the threaded engagement and the distractor support shaft 115 to manipulate the deformable element 113 and arrange the distractor element 110 in the insertion configuration, the working configuration and numerous additional positions therebetween.

When the distractor element 110 of the fourth preferred embodiment is arranged between the superior and inferior spinous processes 25a, 25b, the nut 114 is screwed toward the distal end 116b to compress and/or buckle the deformable element 113 outwardly such that its outer diameter increases in a relatively controlled manner and eventually comes into contact with the superior and inferior spinous processes 25a, 25b. Due to the threading between the nut 114 and the distractor support shaft 115, the nut 114, slider 112, deformable element 113 and distractor support shaft 115 may be selectively locked in various positions to prevent the configuration of the distractor element 110 from unwanted, significant changes. The deformable element 113 may be constructed of a flexible polymer such as silicone, a crushable material such as titanium mesh, a biocompatible rubber material, or nearly any material that is biocompatible, able to take on the general size and shape of the deformable element 113 and withstand the normal operating conditions of the deformable element 113.

Figure 10A:
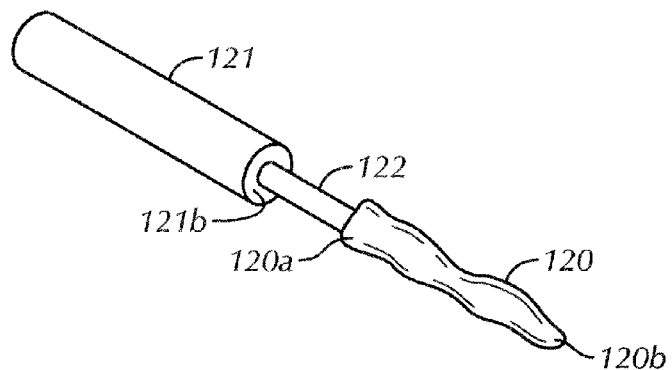
FIG. 10A is a front perspective view of a distractor element in accordance with a fifth preferred embodiment of the present invention, shown in an insertion configuration.
Figure 10B:
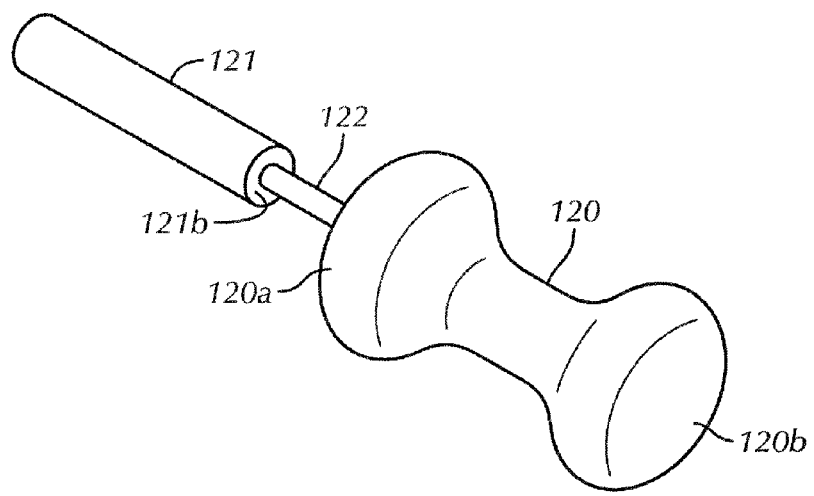
FIG. 10B is a front perspective view of the distractor element of FIG. 10A, shown in a working configuration.

Referring to FIGS. 10A and 10B, in a fifth preferred embodiment, a distractor element 120 is comprised of a balloon 120. The balloon 120 is generally deflated in the insertion configuration (FIG. 10A) and generally inflated in the working configuration (FIG. 10B). For insertion purposes, the balloon 120 is preferably covered and protected by a sleeve 121 that is able to surround the deflated balloon 120 in the insertion configuration and limit folding, movement or damage to the balloon 120 during insertion between the superior and inferior spinous processes 25a, 25b. The distractor element 120 of the fifth preferred embodiment is also preferably associated with an inflation tube 122 secured to the balloon 120 that permits inflation of the balloon 120 from the insertion configuration to the working configuration. The balloon 120 may be inflated by air, a biocompatible liquid, a biocompatible cement or nearly any material that is able to actuate the balloon 120 from the insertion configuration to the working configuration to secure the instrument 1 to the patient's spine 12 and distract the interspinous space ISS. The balloon 120 may be configured to take on nearly any shape in the working configuration, such as a dog bone-shape to generally limit movement of the balloon 120 relative to the superior and inferior spinous processes 25a, 25b in the working configuration. The balloon 120 and/or sleeve 121 may have a tapered nose or distal end 120b, 121b that facilitates insertion of the balloon 120 into the interspinous space ISS during use.

Referring to FIGS. 2A, 2B, 11A and 11B, in a sixth preferred embodiment, a distractor element 130 is comprised of a relatively flat or flattened body having a proximal end 130a, a distal end 130b, a top surface 130c and a bottom surface 103d. The distractor element 130 of the sixth preferred embodiment is preferably constructed of a generally rigid, biocompatible material that is able to take on the general size and shape of the sixth preferred distractor element 130 and withstand the normal operating conditions of the distractor element 130. For example, the distractor element 130 may be constructed of stainless steel, coated aluminum, titanium, PEEK, composites and other metals and polymers. The top and bottom surfaces 130c, 130d of the sixth preferred distractor element 130 are preferably, relatively planar, but are not so limited and my be grooved, tapered, arcuate or otherwise shaped. The top and bottom surfaces 130c, 130d define an insertion thickness $T_I$ of the distractor element 130 that is smaller than a working thickness $T_W$ of the distractor element 130, which is generally measured across the top and bottom surfaces 130c, 130d between points were the superior and inferior vertebrae 25a, 25b are expected to contact the distractor element 130 when inserted in the interspinous space ISS in the working configuration (FIG. 11B).

The distractor element 130 of the sixth preferred embodiment is generally flat or flattened to facilitate insertion of the distractor element 130 into the interspinous space ISS with the top or bottom surfaces 130a, 130b facing the superior or inferior spinous processes 25a, 25b during insertion. Accordingly, the distractor element 130 may be inserted with the top surface 130a facing the superior spinous process 25a and the bottom surface 130b facing the inferior spinous process 25b with significant clearance between the distractor element 130 and the spinous processes 25a, 25b. The distractor element 130 is moved into position in the interspinous space ISS, preferably utilizing fluoroscopy or other imaging techniques, and rotated ninety degrees (90°) such that edges 130e, 130f of the distractor element 130 are in facing engagement or adjacent to the spinous processes 25a, 25b (FIG. 11B) to distract the interspinous space ISS. The edges 130e, 130f may be tapered, rounded, chamfered, grooved or otherwise shaped to facilitate pivoting of the distractor element 130 from the insertion configuration (FIG. 11A) to the working configuration (FIG. 11B).

The preferred distractor element 130 of the sixth embodiment is shown having a generally dumbbell-shape with bulbous proximal and distal ends 130a, 130b to generally limit lateral movement of the distractor element in the working configuration. However, the distractor element 130 is not limited to having a dumbbell-shape and may have nearly any shape that facilitates insertion of the distractor element 130 into the interspinous space ISS and, preferably, pivoting of the distractor element 130 from the insertion configuration to the working configuration. For example, the distractor element may have a triangle-shape, an egg-shape, a generally rectangular-shape, an H-shape, a U-shape or nearly any shape that permits insertion of the distractor element 130 into the interspinous space ISS in the insertion configuration and pivoting of the distractor element 130 about the pivot axis 131 approximately ninety degrees (90°) into the working configuration. The distractor element 130 is also preferably provided to the surgeon as a set of different sized distractor elements 130 having various working thicknesses $T_W$ and insertion thicknesses $T_I$ to facilitate variable patient anatomy, desired distraction between the superior and inferior spinous processes 25a, 25b and other factors that may warrant the use or desire for multiple sized distractor elements 130.

Referring to FIGS. 3-15, the preferred instruments 1 also include an insertion shaft 76 attached to proximal ends 80a, 92a, 102a, 110a, 120a, 130a of the distractor elements 80, 90, 100, 110, 120, 130. The insertion shaft 76 preferably permits insertion of the distractor elements 80, 90, 100, 110, 120, 130 into the interspinous space ISS by urging the distractor elements 80, 90, 100, 110, 120, 130 through the working channel 63 and into the interspinous space ISS utilizing the insertion shaft 76. The preferred insertion shaft 76 is preferably mounted to the frame 50 by a first shaft joint 74, which may be an articulating joint, but is not so limited. The first shaft joint 74 selectively permits the distractor elements 80, 90, 100, 110, 120, 130 to move relative to the frame 50 in certain of the preferred embodiments. The first shaft joint 74 may also be configured for removable mounting of the insertion shaft 76 to the frame 50. In certain of the preferred embodiments of the instrument 1, the first shaft joint 74 is secured to the end of a static bar 58 and permits the insertion shaft 76 to pivot and/or articulate relative to the frame 50, thereby permitting the distractor elements 80, 90, 100, 110, 120, 130 to pivot and move relative to the frame 50. Articulation and movement of the preferred distractor elements 80, 90, 100, 110, 120, 130 relative to the frame 50 permits the surgeon to arrange the instrument 1, as desired, once one of the distractor elements 80, 90, 100, 110, 120, 130 is mounted in the interspinous space ISS. The surgeon is then able to define the preferred working channel 63 with at least the first and second blades 55, 56 and/or the insertion shaft 76.

Figure 14:
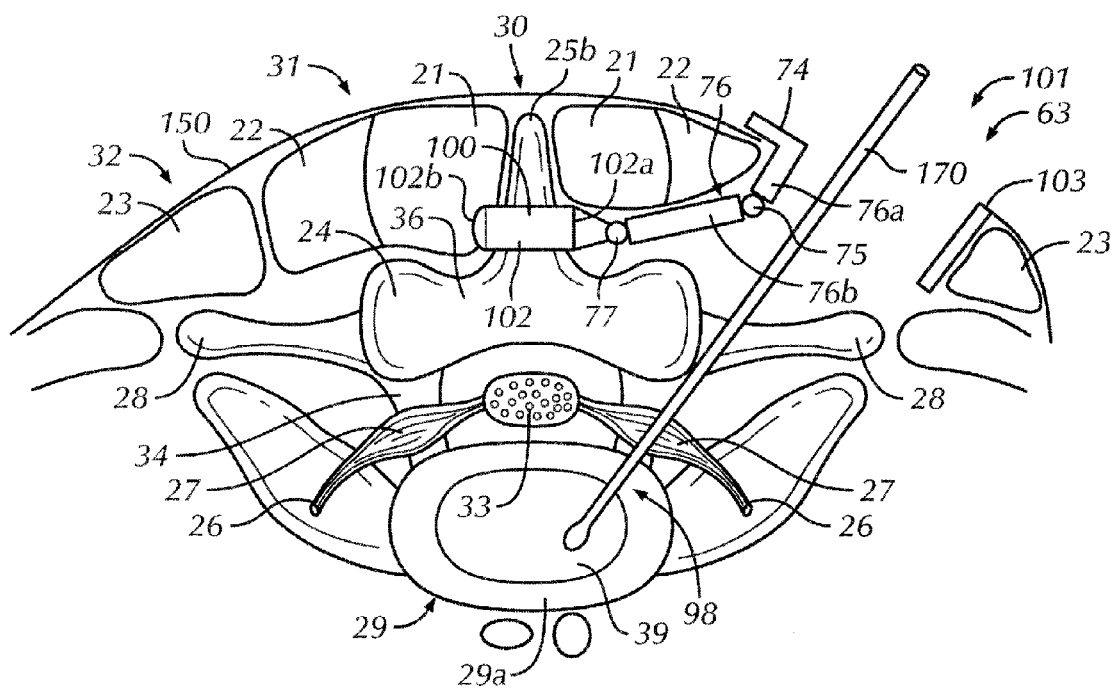
Figure 15:
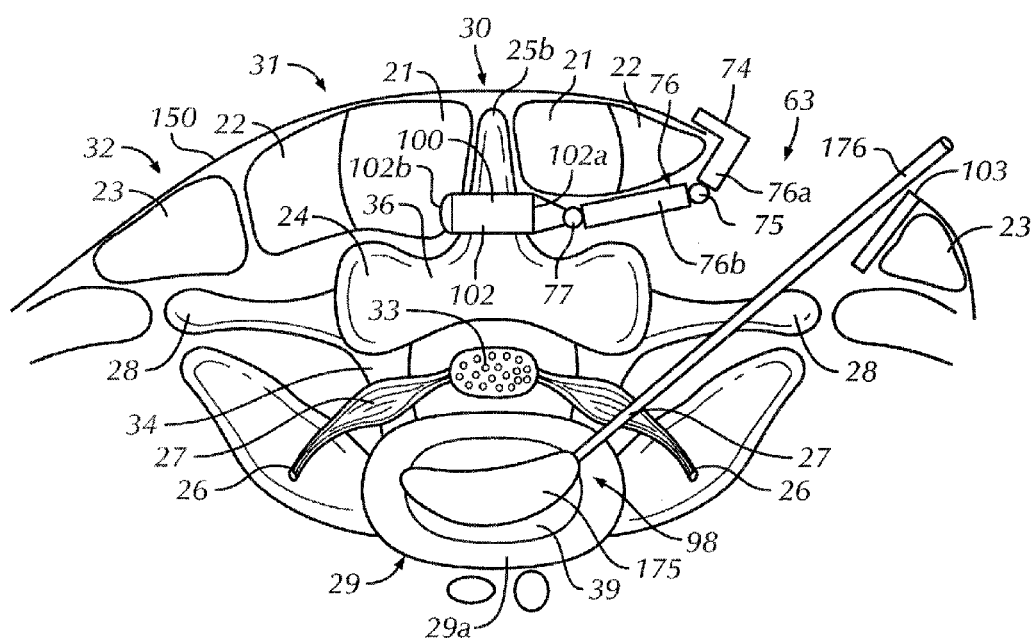

Referring to FIGS. 13-15, the insertion shaft 76 may be utilized as a retractor blade to retract soft tissue and at least partially define the working channel 63 during use. Accordingly, the preferred instruments 1 may be constructed with a frame 50, first blade 55, distractor element 80, 90, 100, 110, 120, 130 and the insertion shaft 76, wherein the first blade 55 and the insertion shaft 76 are utilized to retract soft tissue and define the working channel 63.

Figure 16:
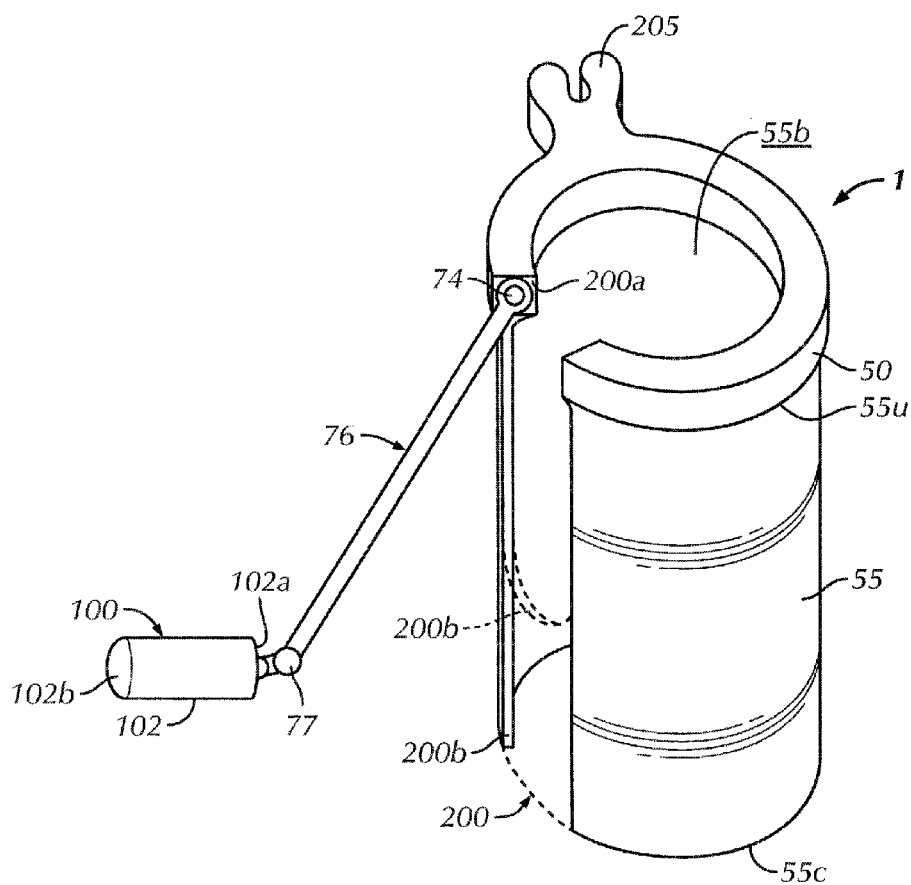
FIG. 16 is a front perspective view of an instrument in accordance with a seventh preferred embodiment of the present invention.

Referring to FIGS. 2A, 2B and 16, in a seventh preferred embodiment, the instrument 1 includes an arcuate frame 50 and the first retractor blade 55 is securely mounted or fixed to the frame 50 at the first attachment joint 55a. The arcuate frame 50 and first retractor blade 55 themselves preferably define a generally rounded or partially circular working channel 63 when inserted into the incision. The first retractor blade 55 of the seventh preferred embodiment preferably has a C-shaped or circular cross-section, but is not so limited. The first retractor blade 55 may be integrally formed with the frame 50 in the seventh preferred embodiment or may be removable therefrom. The first retractor blade 55 of the seventh preferred embodiment may also be longitudinally extendable and/or retractable relative to the frame 50 such that the depth of the working channel 63 may be adjusted for different sized working channels 63 and/or patients. The first retractor blade 55 of the seventh preferred embodiment may also be expandable at a blade distal end 55c such that the working channel 63 may be expanded and/or narrowed near the surgical site 98. For example, the first retractor blade 55 may include sliding panels (not shown), similar to a fan, that permit expansion and contraction of the distal end 55c relative to the frame 50 or may be constructed of a flexible and/or elastic material that permits a surgeon to manipulate the size and shape of the first retractor blade 55 to modify the size of the working channel 63.

The first retractor blade 55 of the seventh preferred embodiment also preferably includes a slot 200 extending from the first attachment joint 55a to the distal end 55c. The slot 200 accommodates mounting of the insertion shaft 76 to the frame 50 at the first shaft joint 74 such that the distractor element 80, 90, 100, 110, 120, 130 may be secured to and movably mounted to the frame 50. The slot 200 does not necessarily extend the entire length of the first retractor blade 55 from a top end 200a to a bottom end 200b at the distal end 55c of the first retractor blade 55. For example, the slot 200 may extend from the frame to a bottom end 200b, which is shown in dashed lines in FIG. 16, along the length of the first retractor blade 55 such that the distal end 55c of the first retractor blade 55 is fully enclosed. Alternatively, the slot 200 may be relatively large, comprising more than half of a semi-circular or C-shape of the first retractor blade 55, as is shown in FIG. 16 and the insertion shaft 76 may be slidable along a portion of the frame 50 for positioning at various sections of the slot 200. In such a configuration, the insertion shaft 76 may be utilized as a retractor blade to retract soft tissue out of the working channel 63 along the slot 200. In any configuration, the slot 200 generally accommodates movement or arrangement of the insertion arm 76 and preferred distractor element 80, 90, 100, 110, 120, 130 relative to the frame 50 such that the distractor element 80, 90, 100, 110, 120, 130 may be inserted into the interspinous space ISS for mounting to the patient 10. The insertion shaft 200 is preferably accommodated by the slot 200 for mounting to the frame 50 and for moving relative to the frame 50.

The instrument 1 of the seventh preferred embodiment also preferably includes a table mount joint 205 extending from the frame 50 that may be utilized to alternatively mount the instrument 1 to the operating table 11 using a conventional table mounting system. The table mount joint 205 is preferably integrally formed with the frame 50 to provide an attachment for a conventional table mount system to engage the instrument of the seventh preferred embodiment in combination with mounting to the patient 10 utilizing the distractor element 80, 90, 100, 110, 120, 130 or as an alternative to mounting to the patient 10.

Referring to FIGS. 3-15, the first shaft joint 74 preferably permits removable mounting of the insertion shaft 76 to the static bar 58 and may also be selectively locked into position. However, the first shaft joint 74 is not limiting and the instrument 1 may be constructed without the first shaft joint 74. For example, the insertion shaft 76 may be constructed of a biocompatible and malleable material that permits a surgeon to bend, shape and/or manipulate the insertion shaft 76 to orient the insertion shaft 76 relative to the distractor element 80, 90, 100, 110, 120, 130 once the distractor element 80, 90, 100, 110, 120, 130 is mounted in the interspinous space ISS in the working configuration. For example, referring to FIGS. 11A and 11B, the insertion shaft 76 is secured to the proximal end 130a of the distractor element 130 of the sixth preferred embodiment. The insertion shaft 76 includes a mounting butt end 134 opposite the distractor element 130 that facilitates attachment of the insertion shaft 76 to the static bar 58. The mounting butt end 134 is preferably mounted to the static bar 58 at the first shaft joint 74. Once the distractor element 130 is positioned in the interspinous space ISS in the working configuration, the insertion shaft 76 may be shaped, bent, twisted or otherwise manipulated by the surgeon, by hand or instrument (not shown), to position the mounting butt end 134 as desired for mounting to the first shaft joint 74 of the static bar 58. The insertion shaft 76 may also be manipulated, due to its malleable nature, to act as a retractor blade, thereby assisting in the definition of the working channel 63. Utilizing the malleable insertion shaft 76 may facilitate one-time use of the insertion shaft 76, such that the insertion shaft 76 and/or distractor element 130 is disposed following a single use. Such a configuration utilizing the malleable insertion shaft 76 is not limited to inclusion with the distractor element 130 of the sixth preferred embodiment and may be adapted for use the any of the other preferred distractor elements 80, 90, 100, 110, 120.

In certain of the preferred embodiments of the instrument 1, the insertion shaft 76 includes a first segment 76a and a second segment 76b. The first segment 76a is preferably secured to the first shaft joint 74 and the second segment 76b is preferably mounted to the first segment 76a at a second articulation joint 75. The second articulation joint 75 also preferably permits articulation between the first and second segments 76a, 76b and is preferably selectively lockable in a desired orientation to create a rigid or semi-rigid connection between one of the distractor elements 80, 90, 100, 110, 120, 130 and the frame 50 in the working configuration. The second articulation joint 75 is not limited to being lockable or to being included in the preferred instrument 1. The second articulation joint 75 is preferred to include additional dimensional articulation between the frame 50 and the distractor elements 80, 90, 100, 110, 120, 130 to provide flexibility in positioning of the insertion shaft 76 through the working channel 63 or to assist in defining the working channel 63.

The distractor elements 80, 90, 100, 110, 120, 130 of the preferred embodiments are preferably mounted to the insertion shaft 76 at an attachment joint 77. The attachment joint 77 also preferably provides articulation and/or rotation between the proximal ends 80a, 102a, 92a, 110a, 122a, 130a of the distractor elements 80, 90, 100, 110, 120, 130 and the insertion shaft 76. The attachment joint 77 is not limited to providing articulation and/or rotation between the insertion shaft 76 and the distractor elements 80, 90, 100, 110, 120, 130, but preferably provide such articulation and/or rotation to provide flexibility for the surgeon in orienting the distractor element 80, 90, 100, 110, 120, 130 relative to the frame 50. Permitting rotation of the distractor elements 80, 90, 100, 110, 120, 130 relative to the insertion shaft 76, particularly to screw the distractor element 90 of the third preferred embodiment into the interspinous space ISS or to otherwise permit multiple orientations of the distractor elements 80, 90, 100, 110, 120, 130 relative to the insertion shaft 76 may also be desirable. The attachment joint 77 is also preferably, but not limited to being lockable in a selected orientation to lock the position of the distractor elements 80, 90, 100, 110, 120, 130 relative to the frame 50 in the working configuration. The attachment joint 77 may also permit rotation of the distractor element 80, 90, 100, 110, 120, 130 relative to the insertion shaft 76. Specifically, in the third preferred embodiment, the attachment joint 77 preferably permits the distractor element 90 to rotate about the longitudinal axis 91 relative to the insertion shaft 76 to facilitate mounting of the distractor element 90 in the interspinous space ISS. The attachment joint 77 also preferably permits removable mounting of each of the preferred distractor elements 80, 90, 100, 110, 120, 130 to the insertion shaft 76. In addition, the removable attachment of the preferred distractor elements 80, 90, 100, 110, 120, 130 from the insertion shaft 76 at the attachment joint 77 may permit the distractor elements 80, 90, 100, 110, 120, 130 to remain as an implant in the interspinous space ISS at the conclusion of a surgery to maintain distraction between the superior and inferior vertebrae.

Referring to FIGS. 1-14, in operation, the preferred instrument 1 is utilized to provide soft tissue retraction and distraction of superior and inferior vertebrae 25a, 25b. To conduct the preferred operation with the preferred instrument 1, the surgeon typically targets the surgical site 98 in the lumbar region of the patient's spine 12. The lumbar region of the patient's spine 12 does not limit the preferred instrument 1, but the preferred instrument 1 is generally configured for conducting procedures in the lumbar region of the patient's spine 12. The surgeon makes an incision through the patient's soft tissue to the surgical site 98, thereby defining the initial working channel 63 from the patient's skin 150 to the surgical site 98. The first and second retractor blades 55, 56 are inserted into the working channel 63 such that distal ends of the first and second retractor blades 55, 56 are positioned near the surgical site 98. One of the preferred distractor elements 80, 90, 100, 110, 120, 130 is inserted through the working channel 63 and into position in the interspinous space ISS between the superior and inferior spinous process 25a, 25b. The distractor element 80, 90, 100, 110, 120, 130 is mounted to the frame 50. The first and second retractor blades 55, 56 are manipulated to expand the working channel 63. The instrument 1 is locked in a preferred orientation while mounted to the patient's spine 12 to permit the surgeon to conduct the surgery through the working channel 63.

The surgeon is preferably able to manipulate the working channel by sliding the slider 53 along the frame 50 relative to the static arm 51, pivoting the first and/or second retractor blades 55, 56 relative to the static arm 51 and sliding arm 52, respectively, and/or manipulating the first shaft joint 74, second articulation joint 75 and/or attachment joint 77 to arrange the distractor element 80, 90, 100, 110, 120, 130 and the insertion shaft 76 relative to the frame 50. This variability of positioning of the first and second retractor blades 55, 56 and the insertion shaft 76 provides significant flexibility for the surgeon in defining a preferred working channel 63 for the surgical procedure.

Referring to FIGS. 3, 3A and 12-14, in the first preferred embodiment, the distal end 102b of the body 102 of the distractor element 100 has a tapered nose to facilitate insertion into the interspinous space ISS. The distal end 102b is not limited to having a tapered nose and may be configured in nearly any arrangement or have any shape that permits insertion into the interspinous space ISS.

Referring to FIGS. 4 and 5, in the second preferred embodiment, the distractor element 80 is expandable from an insertion configuration (FIG. 4) to a working configuration (FIG. 5). In the insertion configuration, the first and second distractor blades 81, 82 are positioned adjacent to each other such that they taper outwardly toward the frame 87. Accordingly, the insertion thickness $T_1$ of the distractor element 80 of the second preferred embodiment is relatively small to facilitate insertion of the distractor element 80 into the interspinous space ISS. Once positioned in the interspinous space ISS, the rotatable screw 87 is tightened, thereby pushing on the blade pivot joint 83 and causing the first and second blade tips 81a, 82a to move away from each other and expand to the working thickness $T_W$ of the distractor element 80. The rotatable screw 86 may be tightened until the desired distraction between the superior and inferior spinous processes 25a, 25b is achieved and the frame 50 is securely mounted to the patient's spine 12. The upper and lower surfaces of the distractor blades 81, 82 may be grooves or otherwise roughened to secure the distractor element 80 to the spinous processes 25a, 25b in the working configuration. The distractor element 80 may subsequently be detached from the instrument 1 at the attachment joint 77 or the rotatable screw 86 may be loosened, thereby drawing the first and second distractor blade tips 81a, 82a toward each other to reduce the profile of the distractor element 80 for removal of the distractor element 80 and instrument 1 from the working channel 63.

In the third preferred embodiment, the threads 93 on the outer surface of the distractor element 90 facilitate rotation or screwing of the distractor element 90 into the interspinous space ISS. The threads 93 are able to engage soft tissue and/or the interspinous processes 25a, 25b and urge the distractor element 90 into the interspinous space ISS. The distractor element 90 of the third preferred embodiment may also be detached from the instrument 1 at the attachment joint 77 such that the distractor element 90 may remain in the interspinous space ISS at the conclusion of the surgery to maintain the distraction and act as a stabilization implant. Alternatively, the distractor element 90 of the third preferred embodiment may be unscrewed or rotated out of the interspinous space ISS for removal from the working channel 63. In addition, the threads 93 may be utilized by the surgeon, in situ, to increase and/or decrease distraction of the interspinous space ISS.

Referring to FIGS. 8 and 9, in the fourth preferred embodiment, the distractor element 110 includes a tapered nose 116b at the distal end 110b and may be expanded to engage the superior and inferior vertebrae 25a, 25b. Once positioned in the interspinous space ISS, the nut 114 is tightened, thereby urging the slider 112 toward the distal end 116b along the distractor support shaft 115 and causing the deformable element 113 to expand to engage the superior and inferior spinous processes 25a, 25b. The nut 114 may be tightened until the distractor element 110 is securely mounted between the superior and inferior spinous processes 25a, 25b and a desired amount of distraction is obtained of the interspinous space ISS. The distractor element 110 of the fourth preferred embodiment may likewise be detached from the insertion shaft 76 at the attachment joint 77 or the nut 114 may be loosened, thereby permitting the deformable element 113 to contract and release from the superior and inferior spinous processes 25a, 25b. Accordingly, the distractor element 110 of the fourth preferred embodiment may be retained in the interspinous space ISS at the conclusion of the surgical procedure or may be removed from the working channel 63 along with the instrument 1.

Referring to FIGS. 10A and 10B, in the fifth preferred embodiment, the distractor element or balloon 120 is inserted into the interspinous space ISS, preferably with the sleeve 121 positioned around the balloon 120. Once positioned within the interspinous space ISS, the sleeve 121 is withdrawn to a position over the inflation tube 122 and a medium is urged into the balloon 120 to expand the balloon 120 from the insertion configuration to the working configuration. The balloon 120 may be inflated using air, bone cement, hydrogel or any material that is able to rearrange the balloon distractor element 120 from the insertion configuration to the working configuration. The balloon distractor element 120 may take on nearly any shape in the working configuration that permits distraction of the interspinous space ISS and securing of the instrument 1 to the patient's spine 12.

Referring to FIGS. 11A and 11B, in the sixth preferred embodiment, the distractor element 130 is inserted into the interspinous space ISS utilizing the insertion shaft 76. The distractor element 130 is inserted such that the top surface 130c is facing the superior spinous process 25a and the bottom surface 130c is facing the inferior spinous process 25b. The distractor element 130 is then rotated ninety degrees (90°) such that the edges 130e, 130f contact or become positioned adjacent to the superior and inferior spinous processes, respectively, thereby providing distraction of the interspinous space ISS. The edges 130e, 130f may be tapered, chamfered, grooved or otherwise configured to facilitate the pivoting movement of the distractor element 130 from the insertion configuration to the working configuration and to secure the distractor element 130 to the spinous processes 25a, 25b in the working configuration. Once the distractor element 130 is in the working configuration, the malleable insertion shaft 76 may be bent, twisted or otherwise manipulated for attachment to the frame 50 and/or to assist in defining the working channel 63 by acting as a retractor blade in retracting soft tissue.

Referring to FIG. 16, in the seventh preferred embodiment, the first retractor blade 55 is inserted into the incision to define the working channel 63. The instrument 1 of the seventh preferred embodiment may be particularly suited for use with sequential dilation, in that the sequentially larger dilators may be initially inserted through the incision to expand the working channel and the first retractor blade 55 may slide over the last dilator tube (not shown) to initially define the working channel 63. The instrument 1 of the seventh preferred embodiment may then be manipulated such that the distractor element 80, 90, 100, 110, 120, 130 is inserted through the working channel 63 defined by the first retractor blade 55 to distract the interspinous space ISS. The insertion shaft 76 may then be manipulated to further expand or define the working channel 63 by manipulating the shape of the malleable insertion shaft 76 and the insertion shaft 76 is secured to the frame 50 at the first shaft joint 74. The first retractor blade 55 may be selectively expanded to expand the working channel 63 and the instrument 1 may be otherwise manipulated to target various surgical sites 98.

At the conclusion of the surgical procedure, the instrument 1 is preferably removed from the working channel 63 and the incision at the patient's skin 150 is closed.

For positioning of the distractor elements 80, 90, 100, 110, 120, 130 in the interspinous space ISS, fluoroscopy may be utilized to verify and/or insure proper positioning between the superior and inferior spinous processes 25a, 25b. The distractor elements 80, 90, 100, 110, 120, 130 may include markers thereon that improve placement and visualization for the surgeon for placement. For example, the preferred distractor elements 80, 90, 100, 110, 120, 130 may include a marker at a position where the devices should be positioned between the superior and inferior spinous processes 25a, 25b in the working configuration.

Referring to FIGS. 1-14, preferred embodiments of the instrument 1 of the present invention are intended for use in the posterior human spine 12. The preferred surgical instrument 1 may be configured with two, three, four (2, 3, 4) or nearly any number of tissue retraction blades 55, 56, 103 and/or the insertion shaft 76 for retraction of soft tissue to define the working channel 63. The preferred first and second blades 55, 56 are oriented to retract tissue cranially and caudally and medially and laterally. Each of the first and second blades 55, 56 is preferably, independently adjustable in both translation and rotation relative to the frame 50. The first and second blades 55, 56 are preferably interlocked and adjusted relative to the frame 50. The first and second blades 55, 56 may be manufactured from known biocompatible materials such as stainless steel, coated aluminum, titanium, PEEK, and other metals and polymers. The cranial and caudal blades 55, 56 preferably have a "closed" position defining a minimum size of the surgical incision and a minimum dilated size through the tissue to initially insert the instrument 1 into the surgical site 98. The length of the first and second blades 55, 56 is generally dictated by the distance from the patient's skin level 150 at the incision site to the boney anatomy at the surgical site 98. The shape of the cranial/caudal blades 55, 56 in the closed position may be circular, triangular or some other shape, and generally have a diameter or major axis of about sixteen millimeters to twenty-two millimeters (16 mm to 22 mm), but are not so limited and may have nearly any diameter or major axis that is able to retract tissue and be inserted into an incision in the patient 10. The material of the preferred first and second blades 55, 56 is generally chosen based on at least two engineering parameters including: 1) to provide adequate stiffness and strength of the first and second blades 55, 56 to retract and retain the tissue being retracted, and 2) to be generally radiolucent so that visual obstruction on x-ray or other visualization mechanisms is minimized.

The cranial and caudal blades 55, 56 may translate up to forty millimeters (40 mm) or more from the closed position. Each blade 55, 56 may also independently rotate up to at least forty degrees (40°), but may also be configured to rotate less or more than forty degrees (40°). Additionally, the rotation may be positive or negative relative to the initial closed position, i.e. the angulation of the blades 55, 56 may be from approximately negative ten degrees to thirty degrees ($-10°$ to $30°$) relative to the closed position. The rotation may be adjusted in discrete increments, for example, by a tooth/pawl mechanism (not shown) or may be infinitely adjustable, for example, by an adjusting screw (not shown). The first and second blades 55, 56 are not limited to any of the particularly specified rotations and/or translations and may be adjustable in nearly any range of rotations and/or translations that are mechanically supportable by the preferred surgical instrument 1.

The cranial and caudal blades 55, 56 may or may not include the first and second blade attachments 103a, 103b on a lower, lateral aspect such that the lateral blade element or tissue shield 103 may be attached at the blade attachments 103a, 103b. The lateral blade element 103 is preferably a thin, flexible membrane that spans from the lower, lateral aspect of the cranial blade 55 to the lower, lateral aspect of the caudal blade 56. The lateral blade element 103 is preferably attached to span across the lower two-thirds (⅔) of the length of the blades 55, 56. The lateral blade element 103 is preferably designed to retract soft tissue laterally below patient skin level 150 to assist in defining the working channel 63. The lateral blade element 103 is preferably flexible so as to allow surgical instruments to deflect the lateral blade element 103 and achieve preferred trajectories to the surgical site 98. The lateral blade element 103 may be manufactured of a flexible, biocompatible polymer such as silicone or nearly any material that is able to take on the generally size and shape of the lateral blade element 103 and withstand the normal operating conditions of the lateral blade element 103.

The lateral blade element 103 may optionally be constructed as a rigid lateral blade 103. The rigid lateral blade element 103 is preferably designed such that it can be inserted and removed interoperatively without changing the position of any other element attached to the frame 50. Ideally, the lateral blade element 103 is positioned subcutaneously and may be adjusted medially and laterally interoperatively, as desired by the surgeon. The lateral blade element 103 may be adapted for use as a nerve root retractor that is rigid or malleable.

The alternative lateral blade element 103 may be mounted to the frame 50 and may translate medially at least up to twenty millimeters (20 mm) relative to the frame 50. The alternative lateral blade element 103 may also rotate or pivot relative to the frame 50 up to fifty degrees (50°). Additionally, the rotation may be positive or negative relative to an initial position, i.e. the angulation of the lateral blade element 103 may be from approximately negative ten degrees to approximately forty degrees ($-10°$ to $40°$). The rotation may be adjusted in discrete increments, for example, by a tooth/pawl mechanism (not shown) or be infinitely adjustable, for example, by an adjusting screw (not shown). The alternative lateral blade element 103 may have an attachment mechanism (not shown) for attachment to one of the preferred distractor elements 100, 80, 90, 110, 120, 130.

The preferred distractor elements 100, 80, 90, 110, 120, 130 generally provide at least two functions, namely: 1) distract the targeted disc space 29 by at least about five millimeters (5 mm) when deployed and 2) attachment to the frame 50 via the insertion shaft 76 so as to securely stabilize the frame 50 to the patient 10 while the disc space 29 is distracted. The insertion shaft 76 may also act as a soft tissue retractor to facilitate expansion or manipulation of the working channel 63, in a manner similar to the above-described alternative lateral blade 103. The interspinous space ISS may be targeted via x-ray fluoroscopy or a guide wire (not shown). The distractor elements 100, 80, 90, 110, 120, 130 are preferably inserted through the unilateral approach incision, with or without the cranial/caudal blades 55, 56 in the incision, and are subcutaneously inserted between targeted, adjacent interspinous processes 25a, 25b. The distractor elements 100, 80, 90, 110, 120, 130 are deployed to preferably provide about five millimeters (5 mm) of distraction of the disc space 29, but are not so limited. The distraction may be more or less than five millimeters (5 mm) depending upon the size of the patient 10, size of the interspinous space ISS or other factors. The distractor elements 100, 80, 90, 110, 120, 130 are then preferably connected to the insertion shaft 76 and rigidly locked into position. The preferred distractor elements 100, 80, 90, 110, 120, 130 thereby acts as the patient mount for the frame 50 while distracting the spinous processes 25a, 25b, thereby increasing the interlaminar space for neurologic decompression and providing distraction of the disc space 29 for a surgical procedure, such as a discectomy and/or interbody implant placement.

Although the preferred surgical instrument 1 may be stabilized by direct attachment to the patient 10 via one of the distractor elements 100, 80, 90, 110, 120, 130 and the insertion shaft 76, the frame 50 may also have an adaptor (not shown) to allow supplemental attachment to the surgical table 11. Such an option may be utilized if one or more of the interspinous processes 25a, 25b is compromised or the surgeon is concerned that the spinous processes 25a, 25b may be damaged by distraction utilizing one of the preferred distractor elements 100, 80, 90, 110, 120, 130.

A preferred example of a surgical method utilizing the surgical instrument 1 of the present application includes:

1) target the surgical site 98; usually posterior to the spine, approximately two to eight centimeters (2-8 cm) from the patient's mid-line depending on surgical procedure, wherein the incision is typically two to four centimeters (2-4 cm) from the mid-line for TLIF procedures and approximately five to eight centimeters (5-8 cm) from the mid-line for ELIF procedures;

2) optionally, a targeting wire may be used to fluoroscopically confirm approach trajectory;

3) making an incision through skin 150 and underlying soft tissue down to the surgical site 98;

4) optionally using a Cobb elevator (or equivalent) to preliminarily release muscular attachments near the zone of retractor deployment;

5) using one or more tissue dilators (not shown) for initial separation of soft tissue;

6) utilizing the preferred surgical instrument 1 by inserting the cranial blade 56, caudal blade 55 and optional lateral shield or blade 103 into the incision over the largest diameter tissue dilator;

7) at least partially separating the cranial and caudal blades 56, 55 to create the preliminary working channel 63 to provide space for final working site preparation and introduction of one of the preferred distractor elements 100, 80, 90, 110, 120, 130;

8) optionally releasing muscular attachments near the zone of retractor deployment;

9) optionally inserting the alternative lateral or medial blade 103 into the preliminary working channel 63 and rotating medially into a desired position;

10) if the optional lateral blade element 103 is not used, a rigid blade (not shown) similar to the cranial and caudal blades 56, 55 may be introduced into the incision and attached to the frame 50;

11) introducing one of the preferred distractor elements 100, 80, 90, 110, 120, 130 into the incision, which may be guided fluoroscopically, through the working channel 63 and into the soft tissue adjacent, targeted spinous processes 25a, 25b;

12) deploying at least the cranial and caudal blades 56, 55 to provide desired expansion of the working channel 63;

13) attaching one of the preferred distraction elements 100, 80, 90, 110, 120, 130 to the insertion shaft 76, manipulating the one of the distraction elements 100, 80, 90, 110, 120, 130 into the interspinous space ISS, manipulating the insertion shaft 76 into a preferred position and locking the one of the distraction elements 100, 80, 90, 110, 120, 130 and insertion shaft 76 to the frame 50 to provide rigid patient mounting;

14) adjusting the cranial and caudal blades 56, 55 and/or the insertion shaft 76 to provide an optimal working channel 63 for surgery;

15) adjusting the preferred surgical instrument 1, interoperatively, to accommodate various surgical sites 98 and/or preferred trajectories;

16) removing and/or adjusting, interoperatively, the cranial and caudal blades 56, 55 and/or the insertion shaft 76 and reattaching different blades and/or implements to modify the working channel 63;

17) conducting the surgical procedure at the surgical site 98;

18) moving the preferred distractor element 80, 110, 120, 130 from the working configuration to the insertion configuration, if appropriate, and manipulating the preferred distractor element 80, 90, 100, 110, 120, 130 and insertion shaft 76 out of the interspinous space ISS and the working channel 63;

18A) alternatively, the preferred distractor element 80, 90, 100, 110, 120, 130 may remain in the working configuration between the interspinous processes 25a, 25b to maintain the distraction by detaching the distractor element 80, 90, 100, 110, 120, 130 from the insertion shaft 76;

19) moving the cranial and caudal blades 56, 55 and any additional equipment into the closed position;

20) removing the preferred instrument 1 from the working channel 63; and 21) closing the incision.

This preferred procedure is in no way limiting, as certain steps may not be performed and additional steps may be added, as the above is a non-limiting example of several surgical steps that may be performed utilizing the preferred surgical instrument 1.

The surgeon preferably, fluoroscopically targets the desired areas for TLIF or ELIF spinal surgeries. The surgeon may use a target wire (not shown) that is radiopaque to assist in targeting. The surgeon generally makes the skin incision and dissects through the fascia and muscle layers to the surgical site 98. After the surgeon has dissected from the skin level 150 to the targeted surgical site 98, muscle may be preliminarily released using a Cobb elevator (or equivalent instrument). One or more tissue dilators (not shown) may be utilized to establish an initial working channel 63 for the insertion of the retractor blades 55, 56. The retractor frame 50 with cranial and caudal blades 56, 55 attached thereto are inserted into the incision (over the final dilator, if used). The static bar 58 and slider 53 are positioned generally toward the patient's midline. The length of the cranial and caudal blades 56, 55 are selected such that, when the blades 55, 56 are fully inserted, the skin level 150 is near the proximal end of the blades 55, 56 and the distal end of the blades 55, 56 are proximate the surgical site 98 near the honey element of the spine 12.

In the working configuration, the distractor element 80, 90, 100, 110, 1120 preferably provides approximately five millimeters (5 mm) of interlaminar and interdiscal distraction, but is not limited to five millimeters (5 mm) of interlaminar and interdiscal distraction, as less or more distraction may be desired and/or provided, based on the patient 10, surgeon preferences or any number of factors. The distractor elements 80, 90, 100, 110, 120, 130 are preferably secured to the frame 50 after being positioned in the working configuration in the interspinous space ISS, but are not so limited and may be secured to the frame 50 prior to insertion into the interspinous space ISS.

The cranial and caudal blades 56, 55 are preferably able to rotate from their vertical orientation (FIG. 12) at a rotation angle of at least approximately negative ten degrees)(−10° to approximately thirty degrees (30°). The rotation angle may be swept independently by each of the cranial and caudal blades 55, 56. In addition, the blades 55, 56 are not limited to these sweep angles and may be pivotable and rotatable through various angles and into various orientations relative to the frame 50 limited only by the mechanical configuration of the preferred instrument 1.

A medial blade (not shown) may alternatively be mounted to the static bar 58 or to a bar (not shown) similar to the static bar 58 and may translate relative to the frame 50 a distance of at least approximately twenty two millimeters (22 mm) and rotate or pivot about a horizontal axis at least from approximately negative ten degrees)(−10° to approximately forty degrees (40°). In such a configuration, the distractor elements 80, 90, 100, 110, 120, 130 may be mounted to the frame 50 utilizing a separate articulating arm (not shown) that extends from the frame 50. The medial blade is not limited to these sweep angles and may be pivotable and rotatable through various angles and into various orientations relative to the frame 50 limited only by the mechanical configuration of the preferred instrument 1

Once the preferred distractor element 80, 90, 100, 110, 120, 130 is secured in the working configuration within the interspinous space ISS, the frame 50, blades 55, 56 and/or insertion shaft 76 may be manipulated to change the location of the working channel 63 to target different surgical sites 98. For example, the working channel 63 may initially be set up for a discectomy and subsequently manipulated by the surgeon to target pedicle screw placement in the pedicle 34.

Referring to FIGS. 13-15, a general surgical instrument 170 is inserted through the deployed surgical instrument 1 into the nucleus pulposis 39 of the lumbar disc 29. The distal end of the surgical instrument 170 is in the proximal side of the disc 29. The preferred surgical instrument 1 is positioned along the ELIF approach trajectory 101. The general surgical instrument 170 may represent any instrument 170 that is intended to perform surgical work in the area of the surgical site 98, such as rongeurs, kerrison rongeurs, pituitary rongeurs, curettes, rasps, shavers, spreaders, impactors, and similar and/or related surgical instruments 170 that are known by those having skill in the art.

The working channel 63 is preferably configured such that the surgeon is able to traversing the disc space 29 to the far, distal side using the general surgical instrument 170. The surgeon may need to access this region of the disc 29 to complete a nucleotomy procedure, release the distal side of the annulus fibrosus 29*a* or perform some other task at this area of the disc 29. In order to achieve this highly oblique instrument trajectory, the lateral blade element 103 is preferably deflectable down and laterally with the shaft of the general surgical instrument 170, without displacing the distractor element 80, 90, 100, 110, 120, 130 or moving the frame 50. Accordingly, extreme access to the disc space 29 may be achieved without requiring adjustment of the instrument 1 interoperatively.

FIG. 15 shows the initial introduction of an interbody implant 175 into the disc space 29. The interbody implant 175 is attached to an inserter shaft 176 for positioning. The interbody implant 175 may be positioned in the disc space 29 once the surgeon removes material from the disc space 29 with the general surgical instrument 170. An inserter shaft 176 of the instrument may impact the lateral blade element 103 during insertion of the interbody implant 175. The interbody implant 175 may be pushed into its final position, preferably centered in the disc space 29. To gain access to this position without releasing the interbody implant 175, the inserter shaft 176 may push against and deflect the lateral blade element 103. Once in final position, the interbody implant 175 may be released from the inserter shaft 176 and the inserter shaft 176 may be removed from the working channel 63.

In an alternate embodiment of the lateral blade element 103, the blade 103 may be constructed of a rigid material such as aluminum, titanium or steel. In this alternate embodiment, the lateral blade element 103 should be designed such that it is predominately subcutaneous and similarly attached to the cranial and caudal blades 56, 55. This alternative embodiment of the lateral blade 103 is preferably designed for interoperative removability, as necessary, to allow the general instrument 170 and inserter shaft 176 to achieve oblique trajectories.

It will be appreciated by those skilled in the art that changes could be made to the embodiments described above without departing from the broad inventive concept thereof. For example, the frame 50 may have a partially flexible configuration such that the frame 50 may be manipulated by the surgeon to modify the working channel 63 or to move into a configuration that limits clutter proximate the incision. In addition, the insertion shaft 76 may be malleable and fixed to at least one of the preferred distractor elements 80, 90, 100, 110, 120, 130 such that the insertion shaft 76 and the one of the distractor elements 80, 90, 100, 110, 120, 130 is a single use instrument that is disposable. It is understood, therefore, that this invention is not limited to the particular embodiments disclosed, but is intended to cover modifications within the spirit and scope of the present invention, as defined by the present description.

We claim:

1. An instrument for spinal surgery for retracting soft tissue and mounting between a superior spinous process and an inferior spinous process, the instrument comprising:
   a frame;
   a first retractor blade mounted to the frame;
   a distractor element movably mounted to the frame, the distractor element having a body, a proximal end and a distal end, the distractor element having an insertion thickness, a working thickness and a length, the working thickness being greater than the insertion thickness, the distractor element configured for mounting between the superior and inferior spinous processes in a working configuration and having a dumbbell-shape in the working configuration, the distractor element being generally tapered at the distal end in an insertion configuration, the distractor element configured for insertion between the superior and inferior spinous processes in the insertion configuration with the insertion thickness positioned between the superior and inferior spinous processes and expandable to the working configuration with the working thickness between the superior and inferior spinous processes, thereby distracting the superior and inferior spinous processes;

an insertion shaft attached to the proximal end, the insertion shaft being malleable; and a first shaft joint mounted between the frame and the insertion shaft.

2. The instrument of claim 1 further comprising:
a second retractor blade, the first retractor blade being a caudal blade and the second retractor blade being a cranial blade; the caudal blade mounted to the frame by a static arm and the cranial blade mounted to the frame by a sliding arm and a sliding fitting, the caudal blade detachably mounted to the static arm by a first attachment joint and the cranial blade mounted to the sliding arm by a second attachment joint, the caudal blade movable relative to the static arm.

3. The instrument of claim 1 wherein the distractor element has a tapered nose at the distal end to facilitate insertion through the soft tissue and between the superior and inferior vertebrae.

4. The instrument of claim 1 further comprising:
a second retractor blade movably mounted to the frame; and
a third retractor blade mounted to the frame.

5. The instrument of claim 4 wherein the third retractor blade is constructed of a relatively flexible material, the third retractor blade mounted to the first retractor blade at a first flexible blade attachment joint and to the second retractor blade at a second flexible blade attachment joint.

6. The instrument of claim 1 wherein the insertion shaft is malleable to facilitate manipulation of the shape and orientation of the insertion shaft after the distractor element is mounted between the superior and inferior spinous processes in the working configuration.

7. The instrument of claim 6 wherein the insertion shaft includes a mounting butt end, the frame including a static bar with a first shaft joint, the mounting butt end removably mountable to the first shaft joint.

8. The instrument of claim 1 wherein the first shaft joint is an articulation joint and the first retractor blade is fixed to the frame.

9. An instrument for spinal surgery for retracting soft tissue and mounting between a superior spinous process and an inferior spinous process, the instrument comprising:
a frame;
a first retractor blade mounted to the frame;
a distractor element movably mounted to the frame, the distractor element having a body, a proximal end and a distal end, the distractor element having an insertion thickness, a working thickness and a length, the working thickness being greater than the insertion thickness, the distractor element having a dumbbell-shape and configured for mounting between the superior and inferior spinous processes in a working configuration, the distractor element being generally tapered at the distal end in an insertion configuration, the distractor element configured for insertion between the superior and inferior spinous processes in the insertion configuration with the insertion thickness positioned between the superior and inferior spinous processes and expandable to the working configuration with the working thickness between the superior and inferior spinous processes, thereby distracting the superior and inferior spinous processes, the working thickness being measured between a first edge that is in contact with the superior spinous process and a second edge that is in contact with the inferior spinous process in the working configuration, the insertion thickness being measured between a top surface and a bottom surface that are oriented substantially perpendicular to the first and second edges;
an insertion shaft attached to the proximal end; and
a first shaft joint mounted between the frame and the insertion shaft.

* * * * *